United States Patent
Yacoby et al.

(10) Patent No.: US 9,181,555 B2
(45) Date of Patent: Nov. 10, 2015

(54) PHOTOCATALYTIC HYDROGEN PRODUCTION AND POLYPEPTIDES CAPABLE OF SAME

(75) Inventors: Iftach Yacoby, Kfar-Hess (IL); Ehud Gazit, Ramat-HaSharon (IL); Nathan Nelson, Tel-Aviv (IL); Itai Benhar, Rechovot (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 1077 days.

(21) Appl. No.: 12/670,407

(22) PCT Filed: Jul. 23, 2008

(86) PCT No.: PCT/IL2008/001018
§ 371 (c)(1),
(2), (4) Date: Jan. 25, 2010

(87) PCT Pub. No.: WO2009/013745
PCT Pub. Date: Jan. 29, 2009

(65) Prior Publication Data
US 2010/0203609 A1    Aug. 12, 2010

Related U.S. Application Data

(60) Provisional application No. 61/064,984, filed on Apr. 7, 2008, provisional application No. 60/935,015, filed on Jul. 23, 2007.

(51) Int. Cl.
*C12N 15/62*    (2006.01)
*C12N 9/02*    (2006.01)
*C12P 3/00*    (2006.01)

(52) U.S. Cl.
CPC .............. *C12N 15/62* (2013.01); *C12N 9/0067* (2013.01); *C12P 3/00* (2013.01)

(58) Field of Classification Search
USPC ........................................ 435/257.1; 800/296
See application file for complete search history.

(56) References Cited

U.S. PATENT DOCUMENTS

| | | |
|---|---|---|
| 4,183,011 A | 1/1980 | Massa |
| 4,211,489 A | 7/1980 | Kleinknecht et al. |
| 4,271,490 A | 6/1981 | Minohara et al. |
| 4,297,607 A | 10/1981 | Lynnworth et al. |
| 4,433,399 A | 2/1984 | Massa |
| 4,501,186 A | 2/1985 | Ikuma |
| 4,554,834 A | 11/1985 | Prinz et al. |
| 4,576,047 A | 3/1986 | Lauer et al. |
| 4,577,506 A | 3/1986 | Poole et al. |
| 4,630,072 A | 12/1986 | Scardovi et al. |
| 4,641,291 A | 2/1987 | Simmons, Sr. et al. |
| 4,672,592 A | 6/1987 | Skinner |
| 4,814,552 A | 3/1989 | Stefik et al. |
| 4,991,148 A | 2/1991 | Gilchrist |
| 5,062,089 A | 10/1991 | Willard et al. |
| 5,138,159 A | 8/1992 | Takase et al. |
| 5,142,506 A | 8/1992 | Edwards |
| 5,245,863 A | 9/1993 | Kajimura et al. |
| 5,372,138 A | 12/1994 | Crawley et al. |
| 5,391,197 A | 2/1995 | Burdette et al. |
| 5,394,741 A | 3/1995 | Kajimura et al. |
| 5,421,338 A | 6/1995 | Crowley et al. |
| 5,432,346 A | 7/1995 | Nose et al. |
| 5,511,043 A | 4/1996 | Lindberg |
| 5,515,853 A | 5/1996 | Smith et al. |
| 5,517,579 A | 5/1996 | Baron et al. |
| 5,519,686 A | 5/1996 | Yanagisawa et al. |
| 5,524,630 A | 6/1996 | Crowley |
| 5,530,683 A | 6/1996 | Lindberg |
| 5,550,791 A | 8/1996 | Peloquin et al. |
| 5,588,432 A | 12/1996 | Crowley |
| 5,682,445 A | 10/1997 | Smith |
| 5,702,629 A | 12/1997 | Cui et al. |
| 5,715,825 A | 2/1998 | Crowley |
| 5,721,721 A | 2/1998 | Yanagisava et al. |
| 5,840,031 A | 11/1998 | Crowley et al. |
| 5,866,856 A | 2/1999 | Holtzman |
| 5,977,958 A | 11/1999 | Baron et al. |
| 6,004,269 A | 12/1999 | Crowley et al. |
| 6,111,565 A | 8/2000 | Chery et al. |
| 6,137,621 A | 10/2000 | Wu |
| 6,147,681 A | 11/2000 | Chery et al. |
| 6,151,014 A | 11/2000 | Zloter et al. |
| 6,169,281 B1 | 1/2001 | Chen et al. |

(Continued)

FOREIGN PATENT DOCUMENTS

| | | |
|---|---|---|
| EP | 0666543 | 8/1995 |
| EP | 1450296 | 8/2004 |

(Continued)

OTHER PUBLICATIONS

Florin, L. et al. Journal of Biochemical Chemistry (Mar. 2, 2001), vol. 276, No. 9; pp. 6125-6132.*
Florin, L. et al. The Journal of Biological Chemistry (Mar. 2, 2001); vol. 276, No. 9, pp. 6125-6132.*
Yacoby et al. PNAS Jun. 7, 2011; vol. 108, No. 23, pp. 9396-9401.*
Attisano et al. "Signal Transduction by the TGF-? Superfamily", Science, 296(5573): 1646-1647, 2002.
Nicolet et al. "Desulfovibrio Desulfuricans Iron Hydrogenase: The Structure Shows Unusual Coordination to an Active Site Fe Binuclear Center", Structure, 7: 13-23, 1999.
Nonaka et al. "Ultrasonic Position Measurement and Its Applications to Human Interface", Instrumentation and Measurement Technology Conference, IMTC/94, Conference Proceedings, 10th Anniversary, Advanced Technologies in I & M, IEEE Hamatsu, Japan, IEEE New York, USA XP010121966, p. 753-756, 1994.

(Continued)

*Primary Examiner* — Russell Kallis

(57) ABSTRACT

An isolated polypeptide comprising a hydrogen generating enzyme attached to a heterologous ferredoxin is disclosed, as well as polynucleotides encoding same, nucleic acid constructs capable of expressing same and cells expressing same. A method for generating hydrogen using the isolated polypeptide is also disclosed.

14 Claims, 8 Drawing Sheets
(6 of 8 Drawing Sheet(s) Filed in Color)

(56) References Cited

U.S. PATENT DOCUMENTS

| | | | |
|---|---|---|---|
| 6,211,863 | B1 | 4/2001 | Chery et al. |
| 6,232,962 | B1 | 5/2001 | Davis et al. |
| 6,252,656 | B1 | 6/2001 | Wu et al. |
| 6,265,676 | B1 | 7/2001 | Zloter et al. |
| 6,282,340 | B1 | 8/2001 | Nasu et al. |
| 6,292,177 | B1 | 9/2001 | Zloter et al. |
| 6,292,180 | B1 | 9/2001 | Lee |
| 6,300,580 | B1 | 10/2001 | Shenholtz et al. |
| 6,367,335 | B1 | 4/2002 | Hicks |
| 6,392,230 | B1 | 5/2002 | Aita |
| 6,392,330 | B1 | 5/2002 | Zloter et al. |
| 6,424,340 | B1 | 7/2002 | Holtzman et al. |
| 6,430,342 | B1 | 8/2002 | Kim et al. |
| 6,485,413 | B1 | 11/2002 | Boppart et al. |
| 6,504,289 | B2 | 1/2003 | Toda et al. |
| 6,577,299 | B1 | 6/2003 | Schiller et al. |
| 6,681,635 | B1 | 1/2004 | Van Schaik |
| 6,724,371 | B1 | 4/2004 | Shenholtz et al. |
| 6,738,408 | B2 | 5/2004 | Abedin |
| 6,745,632 | B1 | 6/2004 | Dryer et al. |
| 6,771,006 | B2 | 8/2004 | Zloter et al. |
| 6,778,735 | B2 | 8/2004 | Miller et al. |
| 6,816,266 | B2 | 11/2004 | Varshneya et al. |
| 6,822,641 | B2 | 11/2004 | Shenholtz et al. |
| 6,823,105 | B2 | 11/2004 | Zloter et al. |
| 6,831,781 | B2 | 12/2004 | Tearney et al. |
| 6,841,742 | B2 | 1/2005 | Shenholtz et al. |
| 6,858,718 | B1 * | 2/2005 | Happe ............... 536/23.2 |
| 6,873,415 | B2 | 3/2005 | Amonette et al. |
| 2002/0031243 | A1 | 3/2002 | Schiller et al. |
| 2003/0095708 | A1 | 5/2003 | Pittel |
| 2003/0142065 | A1 | 7/2003 | Pahlavan |
| 2004/0032399 | A1 | 2/2004 | Sekiguchi et al. |
| 2005/0266541 | A1 * | 12/2005 | Dillon ............... 435/168 |
| 2006/0084157 | A1 | 4/2006 | Happe |
| 2006/0281148 | A1 * | 12/2006 | Swartz et al. ........ 435/69.1 |

FOREIGN PATENT DOCUMENTS

| | | |
|---|---|---|
| GB | 2043899 | 10/1980 |
| GB | 2121174 | 12/1983 |
| TW | 394833 | 6/2000 |
| WO | WO 00/21203 | 4/2000 |
| WO | WO 01/35329 | 5/2001 |
| WO | WO 02/01466 | 1/2002 |
| WO | WO 03/069547 | 8/2003 |
| WO | WO 2004/010592 | 1/2004 |
| WO | WO 2005/072262 | 8/2005 |
| WO | WO 2006/093998 | 9/2006 |
| WO | WO 2009/013745 | 1/2009 |

OTHER PUBLICATIONS

Peters et al. "X-Ray Crystal Structure of the Fe-Only Hydrogenase (CpI) From Clostridium Pasteurianum to 1.8 Angstrom Resolution", Science, 282: 1853-1858, 1998.

Examination Report Dated Sep. 6, 2006 From the Intellectual Property Office of New Zealand Re.: Application No. 535953.

Examination Report Dated Oct. 12, 2005 From the Intellectual Property Office of New Zealand Re.: Application No. 535953.

International Preliminary Report on Patentability Dated Feb. 4, 2010 From the International Bureau of WIPO Re.: Application No. PCT/IL2008/001018.

International Search Report Dated Sep. 22, 2004 From the International Searching Authority Re. Application No. PCT/IL03/00309.

Office Action Dated Jun. 2, 2006 From the State Intellectual Property Office of the People's Republic of China Re.: Application No. 03813673.2.

Translation of the Office Action Dated Sep. 27, 2005 From the National Bureau of Standards, Ministry of Economic Affairs of Taiwan Re.: Application No. 92128407.

Translation of the Official Letter Dated Dec. 17, 2004 From the National Bureau of Standards, Ministry of Economic Affairs of Taiwan Re.: 92128407.

Written Opinion Dated Oct. 30, 2008 From the International Searching Authority Re.: Application No. PCT/IL2008/001018.

Bashton et al. "The Generation of New Protein Functions by the Combination of Domains", Structure, XP005827821, 15(1): 85-99, Jan. 16, 2007.

Ghirardi et al. "Hydrogenases and Hydrogen Photosynthetic Organisms", Annual Review of Plant Biology, XP002497933, 58: 71-91, 2007. Retrieve From the Internet: URL:http://arjournals.annualreviews.org/doi/pdf/10.1146/annurev.arplant.58.032806.
103848>, Online Publication Date: Dec. 6, 2006.

Ihara et al. "Light-Driven Hydrogen Production by a Hybrid Complex of an [NiFe]-Hydrogenase and the Cyanobacterial Photosystem I", Photochemistry and Photobiology, XP002497930, 82(3): 676-682, May 2006.

Ihara et al. "Photoinduced Hydrogen Production by Direct Electron Transfer From Photosystem I Cross-Linked With Cytochrome C3 to [NiFe]-Hydrogenase", Photochemistry and Photobiology, XP002497931, 82(6): 1677-1685, Nov. 2006.

Prince et al. "The Photobiological Production of Hydrogen: Potential Efficiency and Effectiveness as a Renewable Fuel", Critical Reviews in Microbiology, XP008096963, 31(1): 19-31, 2005.

Sheehan et al. "A Look Back at the U.S. Department of Energy's Aquatic Species Program—Biodiesel From Algae", National Renewable Energy Laboratory, NREL/TP-580-24190, 328 P., Jul. 1998.

* cited by examiner

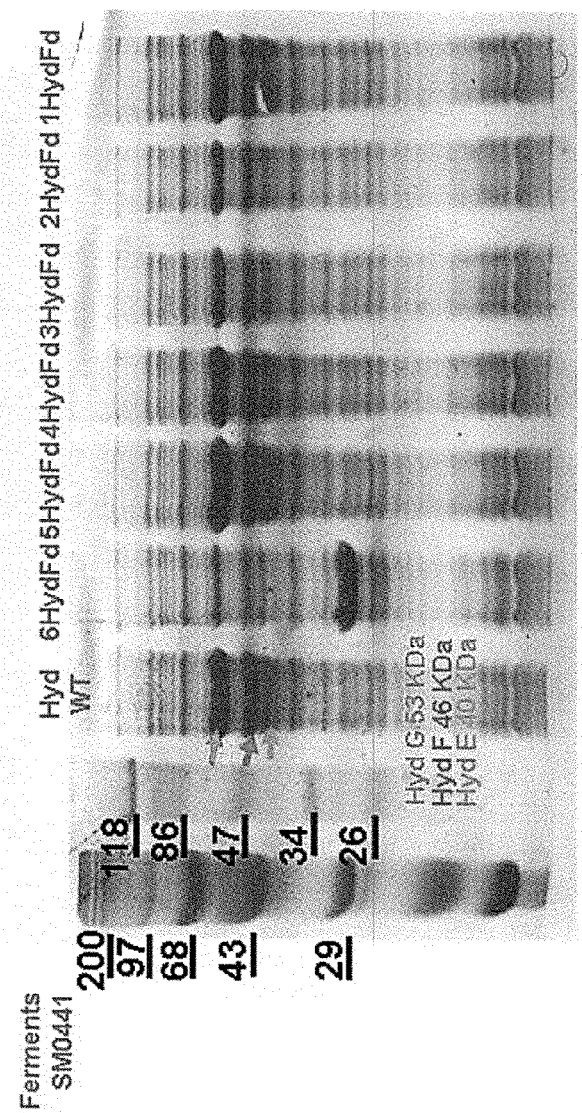

PHOTOCATALYTIC HYDROGEN PRODUCTION AND POLYPEPTIDES CAPABLE OF SAME

RELATED APPLICATIONS

This Application is a National Phase of PCT Patent Application No. PCT/IL2008/001018 having International filing date of Jul. 23, 2008, which claims the benefit of U.S. Provisional Patent Application Nos. 61/064,984, filed on Apr. 7, 2008, and 60/935,015, filed on Jul. 23, 2007. The contents of the above Applications are all incorporated herein by reference.

FIELD AND BACKGROUND OF THE INVENTION

The present invention relates to hydrogen production and, more particularly, to polypeptides capable of same.

The development of a clean, sustainable and economically viable energy supply for the future is one of the most urgent challenges of our generation. Oil production is expected to peak in the near future and economically viable oil reserves are expected to be largely depleted by 2050. A viable hydrogen economy requires clean, sustainable and economic ways of generating hydrogen. Current hydrogen production depends almost entirely on the use of non-renewable resources (i.e. steam reformation of natural gas, coal gasification and nuclear power driven electrolysis of water). Although these approaches are initially likely to drive a transition towards a hydrogen economy, the hydrogen produced is more expensive and contains less energy than the non-renewable energy source from which it is derived. In addition, the use of fossil fuels and nuclear power is unsustainable. Therefore, there is a clear need to establish economically viable means of hydrogen production.

A particularly desirable option is the production of hydrogen using photosynthetic machinery, since the ultimate energy source is solar energy. The twin hearts of the photosynthetic machinery in plants, algae, and cyanobacteria are the two photochemical reaction centers known as Photosystem I (PSI) and Photosystem II (PSII). PSII drives the most highly oxidizing reaction known to occur in biology, splitting water into oxygen, protons and electrons. Oxygen is released into the atmosphere and is responsible for maintaining aerobic life on Earth. The derived electrons are passed along the photosynthetic electron transport chain from PSII via Plastoquinone (PQ) to Cytochrome $b_{6f}$ (cyt $b_{6f}$) and Photosystem I (PSI). From PSI, most of the negative redox potential is stabilized in the form of reduced ferredoxin (Fd) that serves as an electron donor to ferredoxin-NADP$^+$-reductase (FNR) enzyme. Under normal physiological conditions, Fd reduces NADP$^+$ to NADPH via the Fd-FNR complex. In a parallel process (photophosphorylation), protons are released into the thylakoid lumen where they generate a proton gradient that is used to drive ATP production via ATP synthase. NADPH and ATP are subsequently used to produce starch and other biomolecules.

Some green algae and cyanobacteria have evolved the ability to channel the protons and electrons stored in starch into hydrogen production under anaerobic conditions by expressing a hydrogenase enzyme. [Wunschiers, Stangier et al. 2001, Curr Microbiol 42(5): 353-60; Happe and Kaminski 2002, Eur J Biochem 269(3): 1022-32]. The hydrogenase enzyme is localized in the chloroplast stroma and obtains electrons from ferredoxin or flavodoxin that is reduced by Photosystem I and thus competes with FNR for the PSI generated electrons (FIG. 1). However, oxygen is a powerful inhibitor of the hydrogenase enzyme and thus, the generation of hydrogen in these organisms is only transient and also inefficient.

Efforts to generate oxygen-tolerant algal hydrogenases have not met with much success [Seibert et al. 2001, Strategies for improving oxygen tolerance of algal hydrogen production. Biohydrogen II. J. M. Miyake, T.; San Pietro, A., eds, Oxford, UK: Pergamon 67-77]. McTavish et al [J Bacteriol 177(14): 3960-4, 1995] have shown that site-directed mutagenesis of *Azotobacter vinelandii* hydrogenase can render hydrogen production insensitive to oxygen inhibition, but with a substantial (78%) loss of hydrogen evolution activity.

Melis (U.S. Patent Application No. 2001/005343) teaches a process in which the inhibition was lifted by temporally separating the oxygen generating water splitting reaction, catalyzed by PSII, from the oxygen sensitive hydrogen production catalyzed by the chloroplast Hydrogenase (HydA). This separation was achieved by culturing green algae first in the presence of sulfur to build stores of an endogenous substrate and then in the absence of sulfur. This led to inactivation of Photosystem II so that cellular respiration led to anaerobiosis, the induction of hydrogenase, and sustained hydrogen evolution in the light.

The Melis process is, however, subject to considerable practical constraints. The actual rate of hydrogen gas accumulation is at best 15 to 20% of the photosynthetic capacity of the cells [Melis and Happe 2001, Plant Physiol. November; 127(3):740-8] and suffers the inherent limitation that hydrogen production by sulfur deprivation of the algae cannot be continued indefinitely. The yield begins to level off and decline after about 40-70 hours of sulfur deprivation, and after about 100 hours of sulfur deprivation the algae need to revert to a phase of normal photosynthesis to replenish endogenous substrates.

International Publication No. WO 03/067213 describes a process for hydrogen production using *Chlamydomonas reinhardtii* wherein the algae has been genetically modified to down regulate expression of a sulfate permease, CrcpSulP, through insertion of an antisense sequence. This is said to render obsolete prior art sulfur deprivation techniques, as it obviates the need to physically remove sulfur nutrients from growth media in order to induce hydrogen production. The reduced sulfur uptake by the cell using this technique not only results in a substantial lowering of the levels of the major chloroplast proteins such as Rubisco, D1 and the LHCII, but also deprives the cell of sulfur for use in the biosynthesis of other proteins.

Ihara et al (Ihara, Nakamoto et al. 2006; Ihara, Nishihara et al. 2006) teach a fusion protein comprising membrane bound [NiFe] hydrogenase (from the proteobacterium *Ralstonia eutropha* H16) and the peripheral PSI subunit PsaE of the cyanobacterium *Thermosynechococcus elongatus* as a direct light-to-hydrogen conversion system. The isolated hydrogenase-PSI isolated complex displayed light-driven hydrogen production at a rate of [0.58 μmol $H_2$]/[mg chlorophyll] h in vitro. The inefficiency of this system is thought to be derived from the mismatched ability of the hydrogenase to accept electrons compared to the ability of PSI to donate electrons.

Peters et al [Science, 282, 4 Dec., 1998], teach isolation of an Fe-only hydrogenase from *clostridium pasteurianum* which naturally comprises ferredoxin-like structures. Although this hydrogenase is potentially capable of directly generating hydrogen under illuminated conditions, it can not accept electron from PSI since it lacks the native plant structural docking site to do so.

There is thus a widely recognized need for, and it would be highly advantageous to have, a sustainable and efficient process for photosynthetic hydrogen production devoid of the above limitations.

SUMMARY OF THE INVENTION

According to one aspect of the present invention there is provided an isolated polypeptide comprising a hydrogen generating enzyme attached to a heterologous ferredoxin.

According to another aspect of the present invention there is provided an isolated polynucleotide encoding a polypeptide comprising a hydrogen generating enzyme attached to a heterologous ferredoxin via a peptide bond.

According to yet another aspect of the present invention there is provided a nucleic acid construct, comprising an isolated polynucleotide encoding a polypeptide comprising a hydrogen generating enzyme attached to a heterologous ferredoxin via a peptide bond.

According to still another aspect of the present invention there is provided a cell comprising a nucleic acid construct, comprising an isolated polynucleotide encoding a polypeptide comprising a hydrogen generating enzyme attached to a heterologous ferredoxin via a peptide bond.

According to an additional aspect of the present invention there is provided a method of generating hydrogen, the method comprising combining an isolated polypeptide comprising a hydrogen generating enzyme attached to a heterologous ferredoxin with an electron donor so as to generate an electron transfer chain, wherein the electron transfer chain is configured such that the electron donor is capable of donating electrons to the polypeptide thereby generating hydrogen.

According to yet an additional aspect of the present invention there is provided a system comprising an isolated polypeptide comprising a hydrogen generating enzyme attached to a heterologous ferredoxin and an electron donor.

According to still an additional aspect of the present invention there is provided a bioreactor for producing hydrogen, comprising:

a vessel 321, holding a hydrogen producing system, the system comprising a suspension of hydrogen generating enzyme attached to a heterologous ferredoxin and PSI;

a light providing apparatus comprising an optic fiber, the light providing apparatus being configured to provide light of a selected spectrum to the system; and a gas liquid separation membrane for separating gas leaving the suspension from the suspension.

According to further features in the embodiments of the invention described below, the hydrogen generating enzyme is a hydrogenase.

According to still further features in the described embodiments, the hydrogen generating enzyme is a nitrogenase.

According to still further features in the described embodiments, the hydrogenase enzyme is selected from the group consisting of an Fe only hydrogenase, a Ni—Fe hydrogenase and a non-metal hydrogenase.

According to still further features in the described embodiments, the polypeptide further comprises a linker, capable of linking the hydrogen generating enzyme to the ferredoxin.

According to still further features in the described embodiments, the linker is a covalent linker.

According to still further features in the described embodiments, the linker is a non-covalent linker.

According to still further features in the described embodiments, the covalent linker is a peptide bond.

According to still further features in the described embodiments, the polypeptide is as set forth in SEQ ID NOs: 24 or 25.

According to still further features in the described embodiments, the polynucleotide comprises a nucleic acid sequence as set forth in SEQ ID NOs: 1-6.

According to still further features in the described embodiments, wherein the nucleic acid construct further comprises a cis-regulatory element.

According to still further features in the described embodiments, the cis-regulatory element is a promoter.

According to still further features in the described embodiments, the promoter is an inducible promoter.

According to still further features in the described embodiments, the cell is a prokaryotic cell.

According to still further features in the described embodiments, the cell is a eukaryotic cell.

According to still further features in the described embodiments, the prokaryotic cell is a cyanobacteria cell.

According to still further features in the described embodiments, the cell is an algae cell.

According to still further features in the described embodiments, the eukaryotic cell is part of a higher plant.

According to still further features in the described embodiments, the generating hydrogen is effected under anaerobic conditions.

According to still further features in the described embodiments, the electron donor is selected from the group consisting of a biomolecule, a chemical, water, an electrode and a combination of the above.

According to still further features in the described embodiments, the electron donor comprises a biomolecule.

According to still further features in the described embodiments, the biomolecule is light sensitive.

According to still further features in the described embodiments, the light sensitive biomolecule comprises a photocatalytic unit of a photosynthetic organism.

According to still further features in the described embodiments, the photocatalytic unit comprises Photosystem I (PSI).

According to still further features in the described embodiments, a ratio of a polypeptide comprising a hydrogen generating enzyme attached to a heterologous ferredoxin: PSI is greater than 100:1.

According to still further features in the described embodiments, the light sensitive biomolecule comprises rhodopsin.

According to still further features in the described embodiments, the biomolecule is immobilized to a solid support.

According to still further features in the described embodiments, the chemical is selected from the group consisting of dithiothreitol, ascorbic acid, N,N,N',N'-tetramethyl-p-phenylendiamine (TMPD), 2,6-dichlorophenol indophenol and a combination of any of the above.

According to still further features in the described embodiments, the method further comprises illuminating the light sensitive biomolecule following or concomitant with the combining.

According to still further features in the described embodiments, the method further comprises harvesting the hydrogen following the generating.

According to still further features in the described embodiments, the combining is effected in a cell-free system.

According to still further features in the described embodiments, the cell-free system is selected from the group consisting of polymeric particles, microcapsules liposomes, microspheres, microemulsions, nano-plates, nanoparticles, nanocapsules and nanospheres.

According to still further features in the described embodiments, the combining is effected in a cellular system.

According to still further features in the described embodiments, the cellular system is selected from the group consisting of a cyanobacteria, an alga and a higher plant.

According to still further features in the described embodiments, the method further comprises down-regulating an expression of endogenous ferredoxin in the cellular system.

According to still further features in the described embodiments, the biomolecule is comprised in particles.

According to still further features in the described embodiments, the particles are selected from the group consisting of polymeric particles, microcapsules liposomes, microspheres, microemulsions, nanoparticles, nanocapsules, nano-plates and nanospheres.

According to still further features in the described embodiments, the biomolecule is encapsulated within the particle.

According to still further features in the described embodiments, the biomolecule is embedded within the particle.

According to still further features in the described embodiments, the biomolecule is adsorbed on a surface of the particle.

According to still further features in the described embodiments, the system is expressed in cells.

According to still further features in the described embodiments, the cells are selected from the group consisting of cyanobacteria cells, algae cells and higher plant cells.

According to still further features in the described embodiments, the system comprises a suspension of cells.

According to still further features in the described embodiments, the system comprises a suspension of liposomes.

According to still further features in the described embodiments, the spectrum is selected as not to damage the system.

According to still further features in the described embodiments, the spectrum is selected to include activating wavelengths only.

The present invention successfully addresses the shortcomings of the presently known configurations by providing novel polypeptides capable of generating photocatalytically induced hydrogen production.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a schematic diagram illustrating the overall process of native light dependent hydrogen production in algae.

Figure 1:
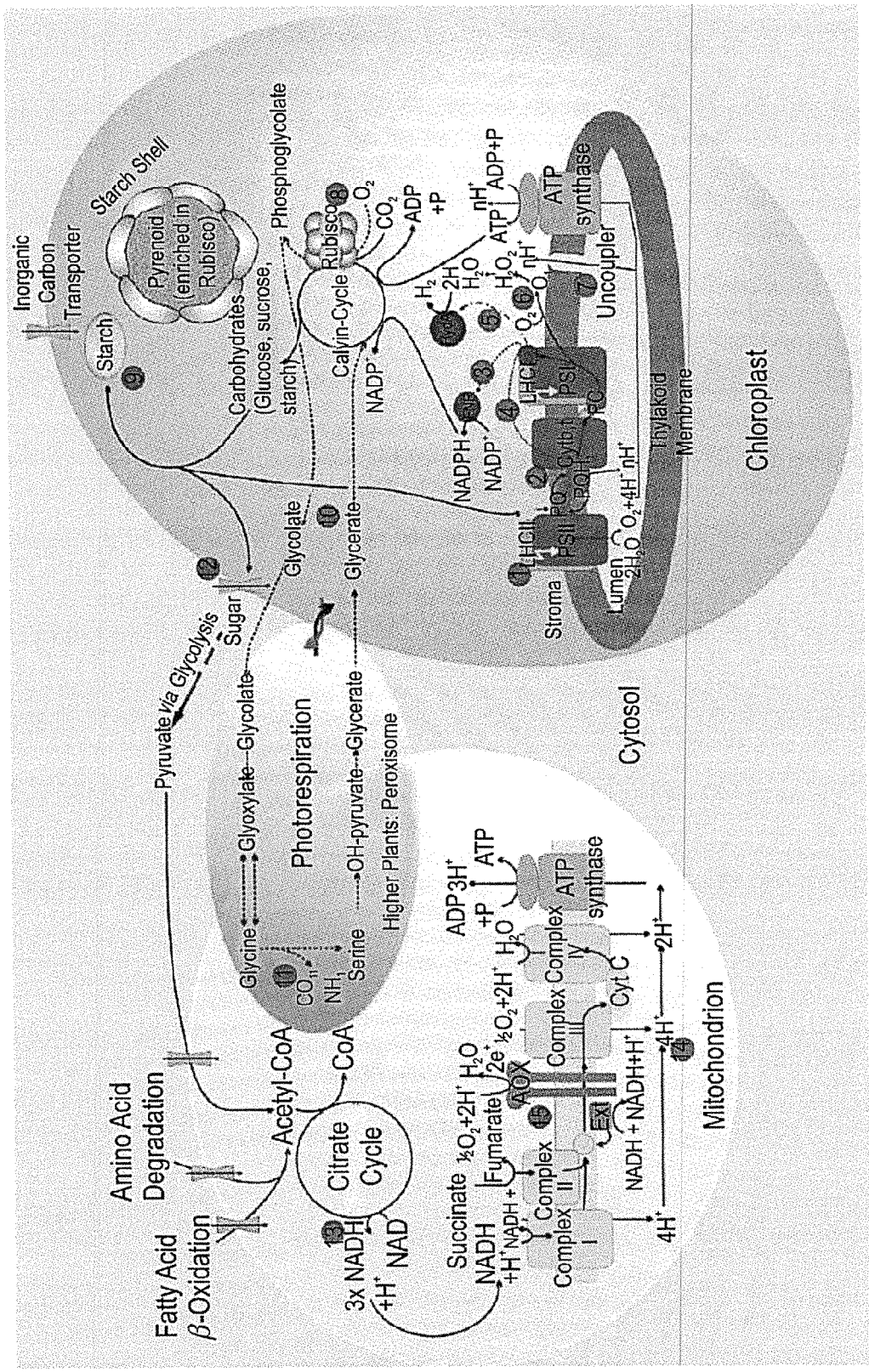
Figures 2A, 2B:
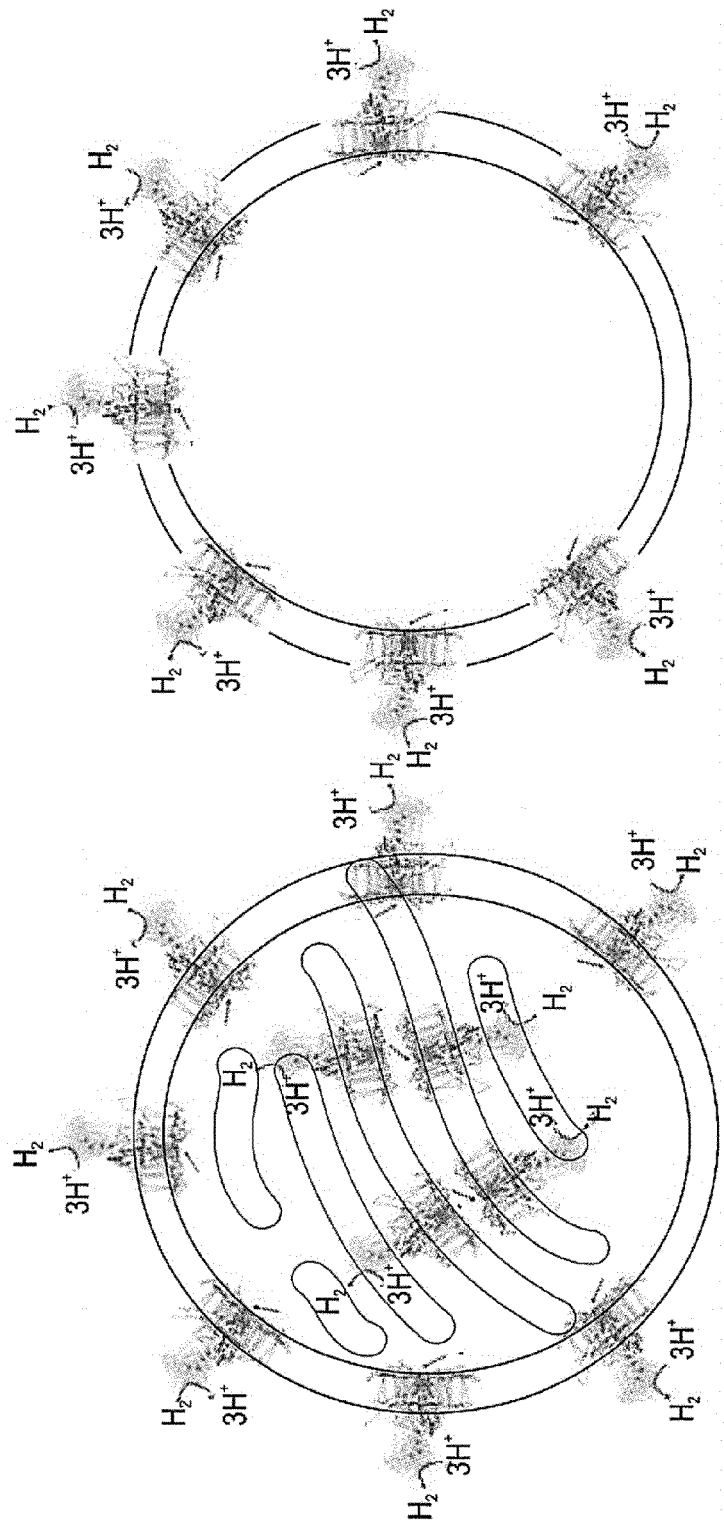

FIGS. 2A-B is a schematic diagram illustrating the position of PSI in multilamellar (FIG. 2A) and unilamellar (FIG. 2B) liposomes.

Figure 3:
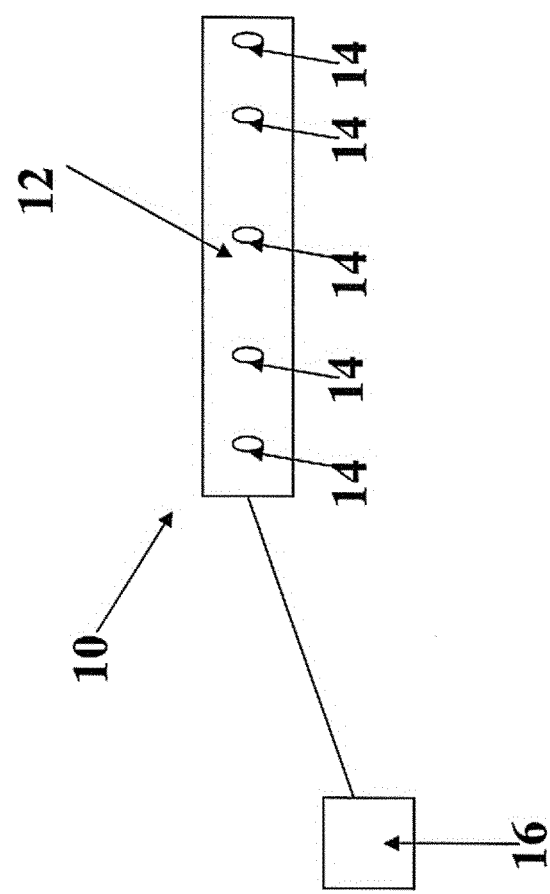

FIG. 3 is a schematic representation of a system for producing hydrogen to an embodiment of the present invention. The figure illustrates a system 10, illustrated comprising an electrode 12 in contact with the polypeptide of the present invention 14. The polypeptide 14 may be attached to the electrode 12 for direct bioelectrocatalysis using any method known in the art such as for example the modification of electrode surfaces by redox mediators or hydrophilic adsorption. Exemplary material that may be used for generating electrode 12 is carbon covered with viologen substituted poly (pyrrole), pyrolytic carbon paper (PC)) and packed graphite columns (PGc). In order to generate hydrogen, the electrode 12 is attached to an electrical source 16.

Figure 4:
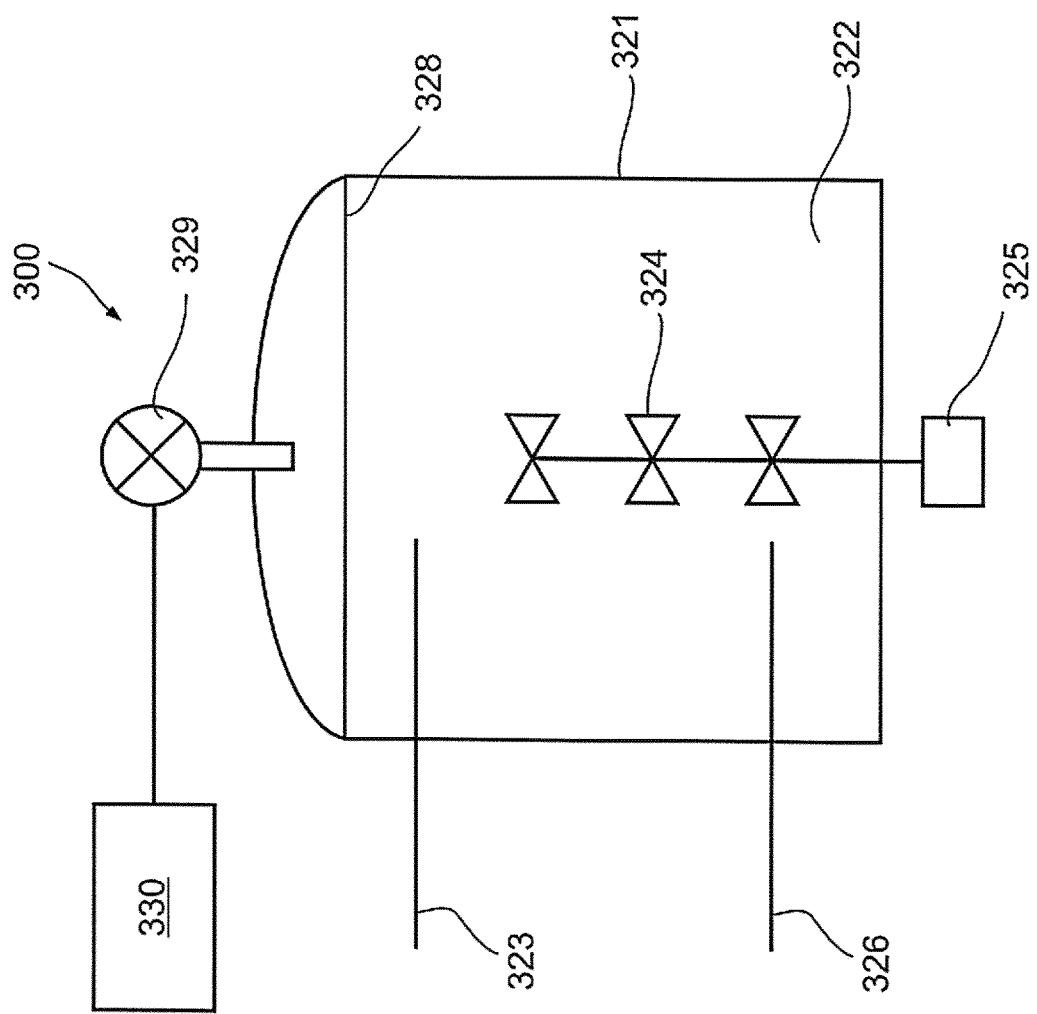

FIG. 4 is a schematic representation of an optic fiber bioreactor according to an embodiment of the present invention. FIG. 4 is a schematic illustration of a reactor 300 for producing hydrogen according to an embodiment of the invention. Reactor 300 comprises a vessel 321 in which the hydrogen producing system comprising PSI, and the ferredoxin unit of the polypeptide of the present invention, are held in a suspension 322. The suspension 322 mays also comprise other components such as sodium citrated and TMPD. The suspension may include the hydrogen producing systems, that is, the PSI and the ferredoxin unit, in any of the above-mentioned ways, for instance, in liposomes on cell culture. Suspension 322 is constantly stirred with stirring blades 324 by rotor 325. The rotor and stirring blade are operated as not to damage the cells or liposomes, but only homogenize them within vessel 321. A temperature control 326 controls the temperature to optimize the activity of the cells or liposomes, for instance 37° C. An optic fiber 323, provides light the cells or liposomes. Hydrogen produced by the hydrogen producing systems bubbles out of the suspension, through a gas-liquid separation membrane 328. From the gas side of membrane 328, the hydrogen is optionally pumped with pump 329 to a hydrogen tank 330.

Figure 5:
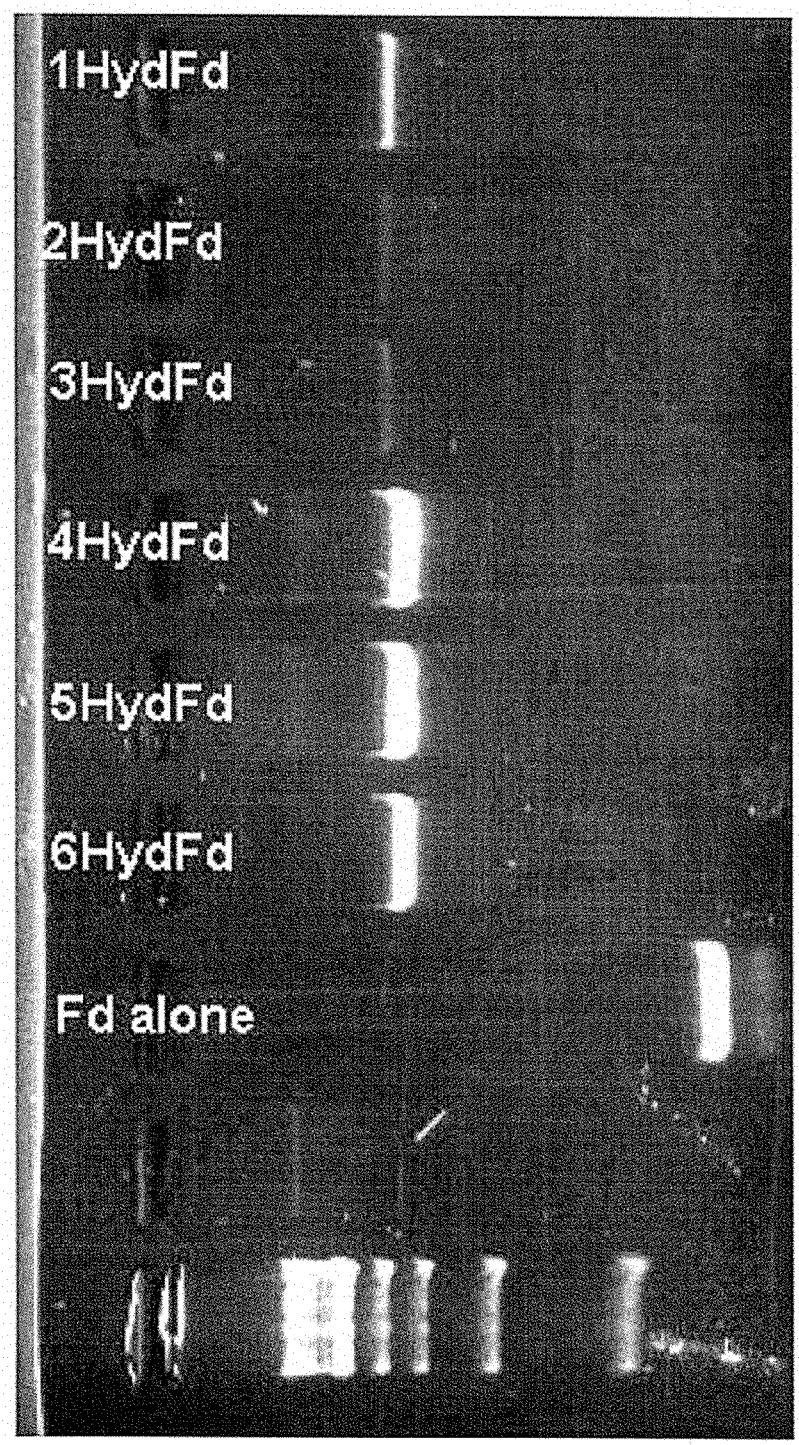

FIG. 5 is a photograph illustrating generation of chimeric fusions of HydA1 and petF genes. 1HydFd- direct linkage of HydA1 and petF; 2HydFd- short linker of four glycine and 1 serine between HydA1 and petF; 3HydFd- medium linker of two repeats of: four glycine and 1 serine between HydA1 and petF; 4HydFd- direct linkage of C-terminus truncated HydA1 and N-terminus truncated petF; 5HydFd- direct linkage of C-terminus truncated HydA1 and petF; 6HydFd- direct linkage of HydA1 and N-terminus truncated petF.

Figures 6A, 6B:
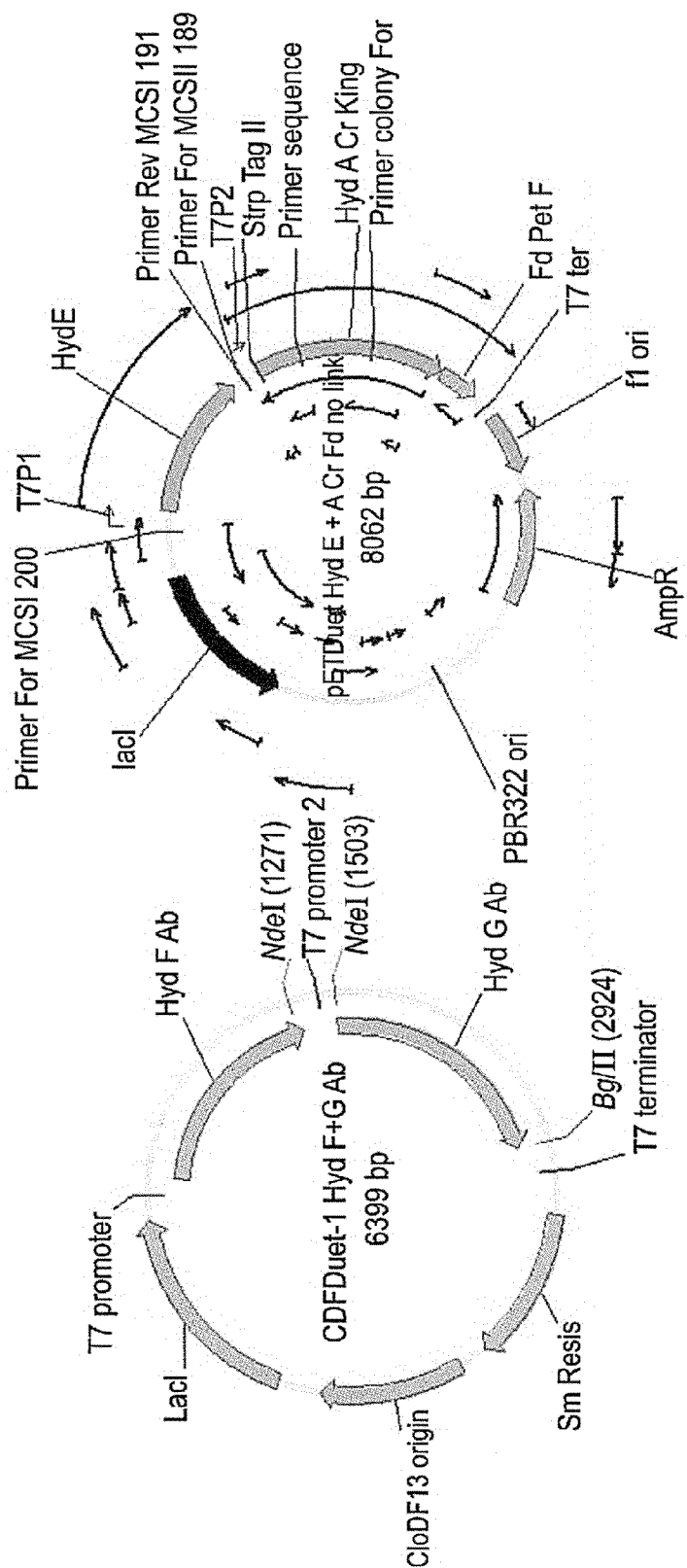

FIGS. 6A-B are maps of exemplary expression constructs used for the expression of the constructs of the present invention.

FIGS. 7A-B are photographs illustrating expression of the polypeptides of the present invention. FIG. 7A—Western analysis using the monoclonal anti StrpTagII (IBA©). In addition, the lower band of native HydA1 was used as internal control. It can be seen that native HydA1 is expressed 10× more than fusion proteins.

FIG. 7B—the 12% polyacrylamide gel shows the accessory proteins HydG/F/E expression pattern which are expressed for all of the chimeras as well as the native hydA1 protein.

Figure 8:
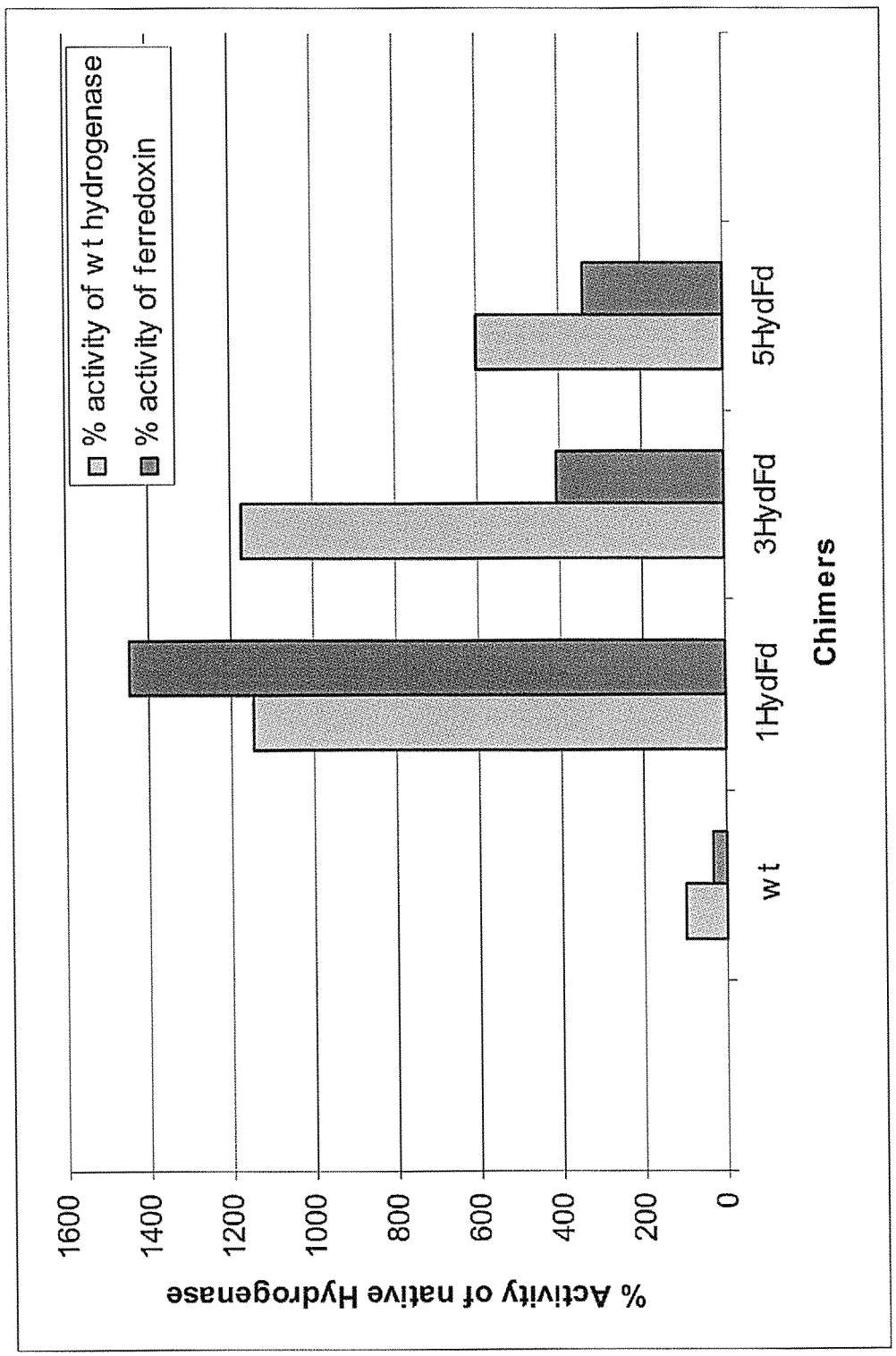

FIG. 8 is a bar graph illustrating hydrogen generation from a total cell extract prepared from *E. coli* cells that express HydA1, Pet F and HydFd chimera. Dithionite was used as electron donor. The experiment was performed in argon atmosphere. Light gray bars: Hydrogen generation by the hydrogenase component alone, as measured by addition of methyl viologen as an electron mediator. Dark gray bars: Ferredoxin-mediated hydrogen production following elimination of methyl viologen from the system. The displayed values of hydrogen production were based on $H_2$ gas production measured by gas chromatography and corrected according to the relative expression level of the proteins according to FIGS. 7A-B.

DESCRIPTION OF THE PREFERRED EMBODIMENTS

The present invention is of a biological method of generating hydrogen and polypeptides capable of catalyzing this reaction.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Molecular hydrogen is a candidate for replacing or supplementing fossil fuels and as a source of clean energy. Natural biological production of hydrogen is based on the presence of hydrogenase enzymes present in certain green algae and photosynthetic bacteria which are capable of accepting electrons from photosystem I (PSI) and conversion thereof into hydrogen gas. The yield of molecular hydrogen from this process is limited because the endogenous electron carriers donate their electrons to destinations other than hydrogenase. For example, reduced electron carriers, such as ferredoxin also donate electrons to ferredoxin-NADP$^+$-reductase (FNR) enzyme.

The present inventors have deduced that in order to increase hydrogen production, electrons must be encouraged to shuttle towards hydrogenase (or other hydrogen generating enzymes, such as nitrogenase) at the expense of the competing processes. The present inventors have contemplated a novel hydrogenase polypeptide which is artificially linked to a heterologous ferredoxin. Such a polypeptide would force the flow of electrons from an electron donor such as photosystem I (PSI) directly to the hydrogenase at the expense of FNR. This novel polypeptide may be expressed in cellular or cell-free systems in order to generate hydrogen gas. Furthermore, the present inventors have conceived that in order to further up-regulate hydrogen production in photosynthetic organisms, the competing process (i.e. the endogenous Fd-FNR complex) is preferably down-regulated.

Whilst reducing the present invention to practice, the present inventors have generated a number of hydrogenase polypeptides, artificially linked to heterologous ferredoxins (FIGS. 7A-B). Such polypeptides were shown to generate hydrogen (FIG. 8) and may also comprise a reduced sensitivity to oxygen.

Thus, according to one aspect of the present invention, there is provided an isolated polypeptide comprising a hydrogen generating enzyme attached to a heterologous ferredoxin.

The phrase "hydrogen generating enzyme" refers to a protein capable of catalyzing a reaction where at least one of the end-products is hydrogen. According to one embodiment the hydrogen generating enzyme is a hydrogenase.

As used herein, the phrase "hydrogenase enzyme" refers to an amino acid sequence of a hydrogenase enzyme with the capability of catalyzing hydrogen oxidation/reduction. Thus the present invention contemplates full-length hydrogenase as well as active fragments thereof. According to one embodiment, the hydrogenase enzyme is a Fe only hydrogenase. According to another embodiment, the hydrogenase is a Ni—Fe hydrogenase. According to yet another embodiment, the hydrogenase is a non-metal hydrogenase. Exemplary hydrogenase enzymes which may be used in accordance with the present invention are set forth by EC 1.12.1.2, EC 1.12.1.3, EC 1.12.2.1, EC 1.12.7.2, EC 1.12.98.1, EC 1.12.99.6, EC 1.12.5.1, EC 1.12.98.2 and EC 1.12.98.3.

Other examples of hydrogenases that may be used according to the teaching of the present invention are listed below in Table 1 together with their source organisms.

TABLE 1

| Source Organism | Protein accession number |
|---|---|
| *Chlamydomonas reinhardtii* | AY055756 |
| *Desulfovibrio vulgaris* hydrogenase | CA26266.1 |
| *Megasphaera elsdenii* | AF120457 |
| *Anabaena variabilis* | CAA55878 |
| *Desulfovibrio Desulfuricans* | 1E3D_A |
| *Clostridium Pasteurianum* | 1FEH_A |
| *Chlamydomonas reinhardtii* | AAR04931 |

According to another embodiment the hydrogen generating enzyme is a nitrogenase enzyme.

As used herein, the phrase "nitrogenase enzyme" refers to an amino acid sequence of a nitrogenase enzyme (EC 1.18.6.1) with the capability of generating hydrogen as a byproduct in a nitrogen fixation reaction. Thus the present invention contemplates full-length nitrogenase as well as active fragments thereof. Examples of nitrogenases that may be used according to the teaching of the present invention are listed below in Table 2 together with their source organisms.

TABLE 2

| Source Organism | Protein accession number |
|---|---|
| *Azotobacter Vinelandii* | 1M1N_A |
| *Clostridium Pasteurianum* | 1MIO_A |
| *Anabaena variabilis* | AAX82499 |

As mentioned the polypeptide of the present invention, comprises a hydrogenase attached to a heterologous ferredoxin.

As used herein, the term "ferredoxin" refers to an amino acid sequence of the iron sulfur protein that is capable of mediating electron transfer to hydrogenase. Thus the present invention contemplates full-length ferredoxin as well as active fragments thereof. According to a preferred embodiment of this aspect of the present invention, the ferredoxin is a plant-type ferredoxin.

Exemplary ferredoxin polypeptides that may be used in accordance with the present invention include, but are not limited to cyanobacterial ferredoxins, algae ferredoxins and non photosynthetic organism ferredoxins.

The qualifier "heterologous" when relating to the ferredoxin indicates that the ferredoxin is not naturally associated with (i.e. endogenous to) the hydrogenase of the present invention. Thus, for example, the phrase "hydrogenase attached to a heterologous ferredoxin" does not comprise the Fe-only hydrogenase from *clostridium pasteurianum*.

The present invention envisages attachment of the heterologous ferredoxin at any position to the hydrogen generating enzyme so long as the hydrogen generating enzyme is capable of generating hydrogen from electrons donated thereto from the attached ferredoxin. The hydrogen generating enzyme and ferredoxin may be linked via bonding at their carboxy (C) or amino (N) termini, or via bonding to internal chemical groups such as straight, branched or cyclic side chains, internal carbon or nitrogen atoms, and the like. Methods of linking the hydrogen generating enzyme to the ferredoxin are further described herein below.

Amino acid sequences of exemplary polypeptides of the present invention are set forth in SEQ ID NOs: 23-28.

The term "polypeptide" as used herein encompasses native polypeptides (either degradation products, synthetically synthesized polypeptides or recombinant polypeptides) and peptidomimetics (typically, synthetically synthesized polypeptides), as well as peptoids and semipeptoids which are polypeptide analogs, which may have, for example, modifications rendering the polypeptides more stable while in a body or more capable of penetrating into cells. Such modifications include, but are not limited to N terminus modification, C terminus modification, polypeptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder. Polypeptide bonds (—CO—NH—) within the polypeptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), polypeptide derivatives (—N(R)—CH2-CO—), wherein R is the "normal" side chain, naturally presented on the carbon atom.

These modifications can occur at any of the bonds along the polypeptide chain and even at several (2-3) at the same time.

Natural aromatic amino acids, Trp, Tyr and Phe, may be substituted for synthetic non-natural acid such as Phenylglycine, TIC, naphthylelanine (Nol), ring-methylated derivatives of Phe, halogenated derivatives of Phe or o-methyl-Tyr.

In addition to the above, the polypeptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 3 and 4 below list naturally occurring amino acids (Table 3) and non-conventional or modified amino acids (Table 4) which can be used with the present invention.

TABLE 3

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 4

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |

TABLE 4-continued

| Non-conventional amino acid | Code | Non-conventional amino acid | Code |
|---|---|---|---|
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α ethylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α thylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |

TABLE 4-continued

| Non-conventional amino acid | Code | Non-conventional amino acid | Code |
|---|---|---|---|
| L-α-methylglutamine | Mgln | L-α-methylglutamate | Mglu |
| L-α ethylhistidine | Mhis | L-α-methylhomophenylalanine | Mhphe |
| L-α thylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α ethylvaline | Mtrp | L-α-methyltyrosine | Mtyr |
| L-α-methylleucine | Mval nbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc | | |

The polypeptides of the present invention are preferably utilized in a linear form, although it will be appreciated that in cases where cyclization does not severely interfere with polypeptide characteristics (e.g. electron transfer), cyclic forms of the polypeptide can also be utilized.

The polypeptide of present invention can be synthesized biochemically. Alternatively, the polypeptide of present invention can be generated using recombinant techniques in order to generate a fusion protein wherein the hydrogen generating enzyme amino acid sequence is attached to the ferredoxin amino acid sequence via a peptide bond or a substituted peptide bond as further described herein above. It will be appreciated that the attachment of the hydrogen generating enzyme to the ferredoxin may also be effected following the independent synthesis (either biochemically, or using recombinant techniques) of hydrogenase (or nitrogenase) and ferredoxin. It addition, the hydrogen generating enzyme and/or ferredoxin may also be isolated from their natural environment and subsequently linked. Each alternative method will be further described herein below.

Biochemical Synthesis

Standard solid phase techniques may be used to biochemically synthesize the polypeptides of the present invention. These methods include exclusive solid phase synthesis, partial solid phase synthesis methods, fragment condensation, classical solution synthesis. These methods are preferably used when the polypeptide cannot be produced by recombinant techniques (i.e., not encoded by a nucleic acid sequence) and therefore involves different chemistry.

Solid phase polypeptide synthesis procedures are well known in the art and further described by John Morrow Stewart and Janis Dillaha Young, Solid Phase Polypeptide Syntheses (2nd Ed., Pierce Chemical Company, 1984).

Synthetic polypeptides can be purified by preparative high performance liquid chromatography [Creighton T. (1983) Proteins, structures and molecular principles. WH Freeman and Co. N.Y.] and the composition of which can be confirmed via amino acid sequencing.

Recombinant Techniques

Recombinant techniques are preferably used to generate the polypeptides of the present invention since these techniques are better suited for generation of relatively long polypeptides (e.g., longer than 20 amino acids) and large amounts thereof, as long as no modified amino acids are included in the sequence. As mentioned, recombinant techniques may be used to generate the hydrogen generating enzyme and ferredoxin independently or alternatively to generate a fusion protein where the hydrogen generating enzyme is attached to the ferredoxin via a peptide bond.

Such recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

To produce the polypeptides of the present invention using recombinant technology, a polynucleotide encoding the polypeptides of the present invention is ligated into a nucleic acid expression vector, which comprises the polynucleotide sequence under the transcriptional control of a cis-regulatory sequence (e.g., promoter sequence) suitable for directing constitutive, tissue specific or inducible transcription of the polypeptides of the present invention in the host cells.

Thus, the present invention contemplates isolated polynucleotides encoding the fusion protein of the present invention.

The phrase "an isolated polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exon sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

Exemplary nucleic acid sequences of the polynucleotides of the present invention are set forth in SEQ ID NOs: 1-6.

As mentioned hereinabove, polynucleotide sequences of the present invention are inserted into expression vectors (i.e., a nucleic acid construct) to enable expression of the recombinant polypeptide. The expression vector of the present invention includes additional sequences which render this vector suitable for replication and integration in prokaryotes, eukaryotes, or preferably both (e.g., shuttle vectors). Typical cloning vectors contain transcription and translation initiation sequences (e.g., promoters, enhances) and transcription and translation terminators (e.g., polyadenylation signals).

A variety of prokaryotic or eukaryotic cells can be used as host-expression systems to express the polypeptides of the present invention. These include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors or transformed with recombinant plasmid expression vectors, such as Ti plasmid, containing the polypeptide coding sequence.

According to one embodiment of this aspect of the present invention, the polynucleotides of the present invention are expressed in a photosynthetic organism. (e.g. higher plant, alga, cyanobacteria) which endogenously express PSI and/or PSII. Advantages thereof are discussed herein below.

Examples of constitutive plant promoters include, but are not limited to CaMV35S and CaMV19S promoters, tobacco mosaic virus (TMV), FMV34S promoter, sugarcane bacilliform badnavirus promoter, CsVMV promoter, Arabidpsisl ACT2/ACT8 actin promoter, Arabidpsis ubiquitin UBQ 1 promoter, barley leaf thionin BTH6 promoter, and rice actin promoter.

An inducible promoter is a promoter induced by a specific stimulus such as stress conditions comprising, for example, light, temperature, chemicals, drought, high salinity, osmotic shock, oxidant conditions or in case of pathogenicity. Examples of inducible promoters include, but are not limited to, the light-inducible promoter derived from the pea rbcS gene, the promoter from the alfalfa rbcS gene, the promoters DRE, MYC and MYB active in drought; the promoters INT, INPS, prxEa, Ha hsp17.7G4 and RD21 active in high salinity and osmotic stress, and the promoters hsr2O3J and str246C active in pathogenic stress.

These constructs can be introduced into plant cells using Ti plasmid, Ri plasmid, plant viral vectors, direct DNA transformation, microinjection, electroporation, Biolistics (gene gun) and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

Various methods can be used to introduce the expression vector of the present invention into the host cell system. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et al. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Transformed cells are cultured under effective conditions, which allow for the expression of high amounts of recombinant polypeptide. Effective culture conditions include, but are not limited to, effective media, bioreactor, temperature, pH and oxygen conditions that permit protein production. An effective medium refers to any medium in which a cell is cultured to produce the recombinant polypeptide of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes and petri plates. Culturing can be carried out at a temperature, pH and oxygen content appropriate for a recombinant cell. In addition, cells of the current invention can be cultured under field conditions such as open ponds, covered ponds, plastic bags (see for example "A Look Back at the U.S. Department of Energy's Aquatic Species Program—Biodiesel from Algae, July 1998, U.S. Department of Energy's Office of Fuels Development, incorporated herein by reference). Such culturing conditions are within the expertise of one of ordinary skill in the art.

Depending on the vector and host system used for production, resultant polypeptides of the present invention may either remain within the recombinant cell, secreted into the fermentation medium, secreted into a space between two cellular membranes, such as the periplasmic space in *E. coli*; or retained on the outer surface of a cell or viral membrane.

It will be appreciated that if the polypeptide of the present invention is to be used in a cell free system, following a predetermined time in culture, recovery of the recombinant polypeptide is effected.

The phrase "recovering the recombinant polypeptide" used herein refers to collecting the whole fermentation medium containing the polypeptide and need not imply additional steps of separation or purification.

Thus, polypeptides of the present invention can be purified using a variety of standard protein purification techniques, such as, but not limited to, salting out (as in ammonium sulfate precipitation), affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

To facilitate recovery, the expressed coding sequence can be engineered to encode the polypeptide of the present invention and fused cleavable moiety. Such a fusion protein can be designed so that the polypeptide can be readily isolated by affinity chromatography; e.g., by immobilization on a column specific for the cleavable moiety. Where a cleavage site is engineered between the polypeptide and the cleavable moiety, the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

The polypeptide of the present invention is preferably retrieved in "substantially pure" form.

As used herein, the phrase "substantially pure" refers to a purity that allows for the effective use of the protein in the applications described herein.

In addition to being synthesizable in host cells, the polypeptide of the present invention can also be synthesized using in vitro expression systems. These methods are well known in the art and the components of the system are commercially available.

Site-Directed Linkage of Hydrogenase to Ferredoxin

Non-natural amino acids may be added to specific places within a recombinant protein followed by chemical conjugation at these specific positions [Chin J W, Cropp T A, Anderson J C, Mukherji M, Zhang Z, Schultz P G. Science. 2003 Aug. 15; 301(5635):964-7; Dieterich D C, Link A J, Graumann J, Tirrell D A, Schuman E M. Proc Natl Acad Sci USA. 2006 Jun. 20; 103(25):9482-7].

Non-Recombinant Linkage of Hydrogenase to Ferredoxin

As mentioned, the hydrogen generating enzyme and the ferredoxin may be generated (e.g. synthesized) or isolated independently and chemically linked one to the other via a covalent (e.g. peptide) or non-covalent linker either directly or via bonding to an intervening linker element, such as a linker peptide or other chemical moiety, such as an organic polymer.

Exemplary chemical crosslinking methods for conjugating the hydrogen generating enzyme with ferredoxin are described herein below:

Thiol-Amine Crosslinking:

In this scheme, the amine group of the hydrogen generating enzyme is indirectly conjugated to a thiol group on the ferredoxin or vice versa, usually by a two- or three-step reaction sequence. The high reactivity of thiols and their relative rarity in most polypeptides make thiol groups ideal targets for controlled chemical crosslinking. Thiol groups may be introduced into one of the two polypeptides using one of several thiolation methods including SPDP. The thiol-containing biomolecule is then reacted with an amine-containing biomolecule using a heterobifunctional crosslinking reagent.

Amine-Amine Crosslinking:

Conjugation of the hydrogen generating enzyme with ferredoxin can be accomplished by methods known to those skilled in the art using amine-amine crosslinkers including, but not limited to glutaraldehyde, bis(imido esters), bis(succinimidyl esters), diisocyanates and diacid chlorides.

Carbodiimide Conjugation:

Conjugation of the hydrogen generating enzyme with ferredoxin can be accomplished by methods known to those skilled in the art using a dehydrating agent such as a carbodiimide. Most preferably the carbodiimide is used in the presence of 4-dimethyl aminopyridine. As is well known to those skilled in the art, carbodiimide conjugation can be used to form a covalent bond between a carboxyl group of one polypeptide and an hydroxyl group of a second polypeptide (resulting in the formation of an ester bond), or an amino group of a second polypeptide (resulting in the formation of an amide bond) or a sulfhydryl group of a second polypeptide (resulting in the formation of a thioester bond).

Likewise, carbodiimide coupling can be used to form analogous covalent bonds between a carbon group of a first polypeptide and an hydroxyl, amino or sulfhydryl group of a second polypeptide. See, generally, J. March, Advanced Organic Chemistry: Reaction's, Mechanism, and Structure, pp. 349-50 & 372-74 (3d ed.), 1985. By means of illustration, and not limitation, the hydrogen generating enzyme may be conjugated to the ferredoxin via a covalent bond using a carbodiimide, such as dicyclohexylcarbodiimide or EDC (1-Ethyl-3-[3-dimethylaminopropyl]carbodiimide Hydrochloride. See generally, the methods of conjugation by B. Neises et al. (1978, Angew Chem., Int. Ed. Engl. 17:522; A. Hassner et al. (1978, Tetrahedron Lett. 4475); E. P. Boden et al. (1986, J. Org. Chem. 50:2394) and L. J. Mathias (1979, Synthesis 561).

Crosslinking of Cysteine Residues

The hydrogen generating enzyme and ferredoxin of the present invention may be linked during a programmed cross linking by the addition of cysteine residues within the sequence of one of the proteins or both. Gentle reduction and oxidation, would then allow the formation of a viable, disulfide linked hydrogenase-ferredoxin complex.

As mentioned, the fusion polypeptide of the present invention is artificially engineered such that the hydrogen generating enzyme comprised within is in an optimal environment for receiving electrons and therefore for generating hydrogen.

Thus, according to another aspect of the present invention, there is provided a method of generating hydrogen. The method comprises combining the fusion polypeptide of the present invention (i.e. the polypeptide comprising the hydrogen generating enzyme and ferredoxin) with an electron donor so as to generate an electron transfer chain.

The phrase "electron donor" as used herein, refers to any biological or non-biological component that is capable of donating electrons. Thus, according to one embodiment of this aspect of the present invention, the electron donor is an electrode. Thus the present invention contemplates a system 10, illustrated herein in FIG. 3 comprising an electrode 12 in contact with the polypeptide of the present invention 14. The polypeptide 14 may be attached to the electrode 12 for direct bioelectrocatalysis using any method known in the art such as for example the modification of electrode surfaces by redox mediators or hydrophilic adsorption. Exemplary material that may be used for generating electrode 12 is carbon covered with viologen substituted poly(pyrrole), pyrolytic carbon paper (PCP) and packed graphite columns (PGC). In order to generate hydrogen, the electrode 12 is attached to an electrical source 16.

According to another embodiment of this aspect of the present invention the electron donor comprises a light-sensitive biomolecule in combination with an electron source.

The term "biomolecule" as used herein refers to a molecule that is or can be produced by a living system as well as structures derived from such molecules. Biomolecules include, for example, proteins, glycoproteins, carbohydrates, lipids, glycolipids, fatty acids, steroids, purines, pyrimidines, and derivatives, analogs, and/or combinations thereof.

According to a preferred embodiment of this aspect of the present invention, the biomolecular electron donor comprises a photocatalytic unit of a photosynthetic organism.

As used herein, the phrase "photocatalytic unit" refers to a complex of at least one polypeptide and other small molecules (e.g. chlorophyll and pigment molecules), which when integrated together work as a functional unit converting light energy to chemical energy. The photocatalytic units of the present invention are present in photosynthetic organisms (i.e. organisms that convert light energy into chemical energy). Examples of photosynthetic organisms include, but are not limited to green plants, cyanobacteria, red algae, purple and green bacteria.

Thus examples of photocatalytic units which can be used in accordance with this aspect of the present invention include biological photocatalytic units such as PS I and PS II, bacterial light-sensitive proteins such as bacteriorhodopsin, photocatalytic microorganisms, pigments (e.g., proflavine and rhodopsin), organic dyes and algae. Preferably, the photocatalytic unit of the present invention is photosystem I (PS I).

PSI is a protein-chlorophyll complex, present in green plants and cyanobacteria, that is part of the photosynthetic machinery within the thylakoid membrane. It is ellipsoidal in shape and has dimensions of about 9 by 15 nanometers. The PS I complex typically comprises chlorophyll molecules which serve as antennae which absorb photons and transfer the photon energy to P700, where this energy is captured and utilized to drive photochemical reactions. In addition to the P700 and the antenna chlorophylls, the PSI complex contains a number of electron acceptors. An electron released from P700 is transferred to a terminal acceptor at the reducing end of PSI through intermediate acceptors, and the electron is transported across the thylakoid membrane.

Examples of PSI polypeptides are listed below in Table 5 together with their source organisms.

TABLE 5

| Source Organism | Protein accession number |
|---|---|
| *Amphidinium carterae* | CAC34545 |
| *Juniperus chinensis* | CAC87929 |
| *Cedrus libani* | CAC87143 |
| *Spathiphyllum* sp. SM328 | CAC87924 |
| *Persea americana* | CAC87920 |
| *Zamia pumila* | CAC87935 |
| *Ophioglossum petiolatum* | CAC87936 |
| *Taxus brevifolia* | CAC87934 |
| *Afrocarpus gracilior* | CAC87933 |
| *Pinus parviflora* | CAC87932 |
| *Picea spinulosa* | CAC87931 |
| *Phyllocladus trichomanoides* | CAC87930 |
| *Serenoa repens* | CAC87923 |
| *Saururus cernuus* | CAC87922 |
| *Platanus racemosa* | CAC87921 |
| *Pachysandra terminalis* | CAC87919 |
| *Nymphaea* sp. cv. Paul Harriot | CAC87918 |
| *Nuphar lutea* | CAC87917 |
| *Nelumbo nucifera* | CAC87916 |
| *Acer palmatum* | CAD23045 |
| *Cupressus arizonica* | CAC87928 |
| *Cryptomeria japonica* | CAC87927 |
| *Abies alba*] | CAC87926 |
| *Gnetum gnemon* | CAC87925 |
| *Magnolia grandiflora* | CAC87915 |
| *Liquidambar styraciflua* | CAC87914 |
| *Lilium brownii* | CAC87913 |
| *Isomeris arborea* | CAC87912 |
| *Fagus grandifolia* | CAC87911 |
| *Eupomatia laurina* | CAC87910 |
| *Enkianthus chinensis* | CAC87909 |
| *Coptis laciniata* | CAC87908 |
| *Chloranthus spicatus* | CAC87907 |
| *Calycanthus occidentalis* | CAC87906 |
| *Austrobaileya scandens*] | CAC87905 |
| *Amborella trichopoda* | CAC87904 |
| *Acorus calamus* | CAC87142 |

The photosystem I complex may be in the native cellular membrane along with photosystem II and the rest of the photosynthetic electron transport chain, or it can be provided in a detergent-solubilized form. Methods for isolating native membranes from photosynthetic organisms are known in the art and a preferred method is provided in the publication of (Murata 1982, Plant Cell Physiol 23: 533-9). Purified thylakoids may be quantitated and expressed as a particular amount of chlorophyll. Methods for quantitating chlorophyll are known for example as set forth by (Amon 1949, Plant Physiol 24(1): 1-15). Methods for obtaining isolated photosystem I in a detergent solubilized form is also known and an exemplary method is disclosed by (Evans, Sihra et al. 1977, Biochem J 162(1): 75-85).

According to one embodiment, the light sensitive biomolecule is immobilized on a solid support. WIPO PCT Application WO2006090381, incorporated herein by reference, teaches immobilization of PS-I on a solid supports such as metal surfaces by genetic manipulation thereof.

As mentioned hereinabove, in order for light sensitive biomolecules to act as electron donors they typically act in combination with an electron source. Exemplary electron sources that may be used in combination with PSI include sodium dithionite (e.g. at about 5 mM), dithiothreitol (e.g. at about 50 mM) and a combination of dithiothreitol plus ascorbic acid (e.g. at about 2 mM ascorbic acid). According to one embodiment PSI is used in combination with PSII, where the latter serves as an intermediate, passing electrons from the electron source to PSI. In this case, the electron source may be water. Other electron sources that may be used according to the teachings of the present invention include, but are not limited to N,N,N',N'-tetramethyl-p-phenylendiamine (TMPD) and 2,6-dichlorophenol indophenol.

As mentioned, the ferredoxin-hydrogenase (or ferredoxin-nitrogenase) fusion protein of the present invention is preferably not inhibited by the presence of dissolved oxygen (or at least, comprise a reduced sensitivity to oxygen). Such fusion proteins may survive in the atmosphere for approximately ~300 seconds ($IC_{50}$) in comparison to 1 sec of native *Chlimydomonas renhardtii* hydrogenase. However, if the ferredoxin-hydrogenase fusion protein of the present invention is inhibited by dissolved oxygen, it may be necessary to remove oxygen from the reaction mixture. The removal of oxygen can be performed in a number of ways. For example, if dithionite or high concentrations of dithiothreitol (e.g., 50 mM dithiothreitol) are used as electron donors, these will react with dissolved oxygen to remove it. If water is used as an electron donor in cellular systems, oxygen will be produced by photosystem II and 5 mM glucose plus the over-expression/or the external addition of glucose oxidase (3 µg/ml, Sigma, St. Louis, Mo.) can be included in the reaction mix to rapidly remove oxygen as it is produced.

As mentioned herein above, the method of the present invention envisages combining the fusion protein of the present invention with an electron donor in such a way so as to promote electron transfer from the donor to the fusion protein.

As used herein, the term "combining" refers to any method where the fusion protein and the electron donor are in close enough proximity that electron transfer from the latter to the former occurs. Thus, the term "combining" incorporates such methods as co-expressing and co-solubilizing the fusion protein and electron donor of the present invention.

According to one embodiment, the fusion protein and electron donor are combined in a cellular system. Thus, for example the fusion protein may be expressed in a photosynthetic organism where PSI and optionally PSII are endogenously expressed.

Preferably, the amount of fusion protein is adjusted for maximal optimization of the system. Thus, according to an embodiment of this aspect of the present invention, a ratio of fusion protein:PSI is greater than 100:1, more preferably greater than 500:1 and even more preferably greater than 1000:1. Preferably, the cellular system is forced to respirate under unaerobic conditions so as to avoid the generation of oxygen.

In order for PSI to transfer electrons to the ferredoxin unit of the polypeptide of the present invention, preferably PSI is energized using light energy. The illuminating may proceed following or concomitant with the expression of the fusion protein of the present invention. A bioreactor may be used which excludes high energy wavelength such as UV radiation, and enables the entrance of the visible red which exclusively feeds and ignite the PSI. An exemplary bioreactor that may be used in accordance with the teachings of the present invention is illustrated in FIG. 3.

FIG. 4 is a schematic illustration of a reactor 300 for producing hydrogen according to an embodiment of the invention. Reactor 300 comprises a vessel 321, in which the hydrogen producing system comprising PSI, and the ferredoxin unit of the polypeptide of the present invention, are held in a suspension 322. The suspension 322 may also comprise other components such as sodium citrated and TMPD. The suspension may include the hydrogen producing systems, that is, the PSI and the ferredoxin unit, in any of the above-mentioned ways, for instance, in liposomes or in cell culture. Suspension 322 is constantly stirred with stirring blades 324 by rotor 325. The rotor and stirring blade are operated as not to damage the cells or liposomes, but only homogenize them within vessel 321.

A temperature control 326 controls the temperature to optimize the activity of the cells or liposomes, for instance, 37° C.

An optic fiber 323, provides light to the cells or liposomes. Preferably, the light provided by fiber 323 is free of damaging wavelengths, such as UV. Optionally, the light is also free of non-activating wavelengths, for instance, green light. Hydrogen produced by the hydrogen producing systems bubbles out of the suspension, through a gas-liquid separation membrane 328. From the gas side of membrane 328, the hydrogen is optionally pumped with pump 329 to a hydrogen tank 330.

As mentioned herein above, the endogenous electron transport system in all photosynthetic organisms comprises donation of electrons from ferredoxin to ferredoxin-$NADP^+$-reductase (FNR). In order to divert the flow of electrons away from this competing enzyme, the present invention contemplates down-regulation thereof.

The phrase "ferredoxin-$NADP^+$-reductase" as used herein refers to the enzyme as set forth by EC 1.18.1.2. present in photosynthetic organisms.

Downregulation of FNR may be effected on the genomic level (using classical genetic approaches) and/or the transcript level. This may be achieved using a variety of molecules which interfere with transcription and/or translation (e.g., antisense, siRNA, Ribozyme, DNAzyme).

Following is a list of agents capable of downregulating expression level of FNR.

One agent capable of downregulating a FNR is a small interfering RNA (siRNA) molecule. RNA interference is a two step process. The first step, which is termed as the initiation step, input dsRNA is digested into 21-23 nucleotide (nt) small interfering RNAs (siRNA), probably by the action of Dicer, a member of the RNase III family of dsRNA-specific ribonucleases, which processes (cleaves) dsRNA (introduced directly or via a transgene or a virus) in an ATP-dependent manner. Successive cleavage events degrade the RNA to 19-21 bp duplexes (siRNA), each with 2-nucleotide 3' overhangs [Hutvagner and Zamore Curr. Opin. Genetics and Development 12:225-232 (2002); and Bernstein Nature 409: 363-366 (2001)].

In the effector step, the siRNA duplexes bind to a nuclease complex to from the RNA-induced silencing complex (RISC). An ATP-dependent unwinding of the siRNA duplex is required for activation of the RISC. The active RISC then targets the homologous transcript by base pairing interactions and cleaves the mRNA into 12 nucleotide fragments from the 3' terminus of the siRNA [Hutvagner and Zamore Curr. Opin. Genetics and Development 12:225-232 (2002); Hammond et al. (2001) Nat. Rev. Gen. 2:110-119 (2001); and Sharp Genes. Dev. 15:485-90 (2001)]. Although the mechanism of cleavage is still to be elucidated, research indicates that each RISC contains a single siRNA and an RNase [Hutvagner and Zamore Curr. Opin. Genetics and Development 12:225-232 (2002)].

Because of the remarkable potency of RNAi, an amplification step within the RNAi pathway has been suggested. Amplification could occur by copying of the input dsRNAs which would generate more siRNAs, or by replication of the siRNAs formed. Alternatively or additionally, amplification could be effected by multiple turnover events of the RISC [Hammond et al. Nat. Rev. Gen. 2:110-119 (2001), Sharp Genes. Dev. 15:485-90 (2001); Hutvagner and Zamore Curr. Opin. Genetics and Development 12:225-232 (2002)]. For more information on RNAi see the following reviews Tuschl ChemBiochem. 2:239-245 (2001); Cullen Nat. Immunol. 3:597-599 (2002); and Brantl Biochem. Biophys. Act. 1575: 15-25 (2002).

Synthesis of RNAi molecules suitable for use with the present invention can be effected as follows. First, the FNR mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (www.ambion.com/techlib/tn/91/912.html).

Second, potential target sites are compared to an appropriate genomic database (e.g., plant or bacteria etc.) using any sequence alignment software, such as the BLAST software available from the NCBI server (www.ncbi.nlm.nih.gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

RNAi has been successfully used in plants for down-regulation of proteins—see for example Moritoh et al., Plant and Cell Physiology 2005 46(5):699-715.

Another agent capable of downregulating FNR is a DNAzyme molecule capable of specifically cleaving an mRNA transcript or DNA sequence of the FNR. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al.

Downregulation of a FNR can also be effected by using an antisense polynucleotide capable of specifically hybridizing with an mRNA transcript encoding the FNR. Design of antisense molecules which can be used to efficiently downregulate a FNR must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

Algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

In addition, several approaches for designing and predicting efficiency of specific oligonucleotides using an in vitro system were also published (Matveeva et al., Nature Biotechnology 16: 1374-1375 (1998)].

For more information pertaining to the inhibition of gene expression in plant cells by expression of antisense RNA, see for example Joseph R. Ecker and Ronald W. Davis, PNAS, 1986, vol. 83, no. 15, 5372-5376.

Thus, the current consensus is that recent developments in the field of antisense technology which, as described above, have led to the generation of highly accurate antisense design algorithms and a wide variety of oligonucleotide delivery systems, enable an ordinarily skilled artisan to design and implement antisense approaches suitable for down-regulating expression of known sequences without having to resort to undue trial and error experimentation.

Another agent capable of downregulating a FNR is a ribozyme molecule capable of specifically cleaving an mRNA transcript encoding FNR. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications.

Yet another agent capable of downregulating FNR would be any molecule which binds to and/or cleaves FNR. Such molecules can be FNR antagonists, or FNR inhibitory peptide.

It will be appreciated that a non-functional analogue of at least a catalytic or binding portion of FNR can be also used as an agent which downregulates FNR.

Another agent which can be used along with the present invention to downregulate FNR is a molecule which prevents FNR activation or substrate binding.

As mentioned, the fusion protein and electron donor may also be combined in a non-cellular system.

In one embodiment the components of the present invention are suspended in a buffered aqueous solution at a pH at which both the photosynthetic components (e.g. PSI) and ferredoxin-hydrogenase fusion protein are active (for example, in a solution of about 2 mM to about 500 mM Tris-HCl, pH 8.0, preferably 30 mM Tris-HCl to 100 mM Tris-HCl, and preferably about 40 mM Tris-NCl), at a temperature at which both the fusion protein of the present invention and the photosynthetic components are active (generally about 10° C. to about 40° C.), and with an appropriate electron donor.

In one embodiment, the fusion protein of the present invention and the electron donor are encapsulated in a carrier system (i.e., encapsulating agent) of desired properties. In a specific embodiment, the encapsulating agent is a liposome.

As used herein and as recognized in the art, the term "liposome" refers to a synthetic (i.e., not naturally occurring) structure composed of lipid bilayers, which enclose a volume. Exemplary liposomes include, but are not limited to emulsions, foams, micelles, insoluble monolayers, liquid crystals, phospholipid dispersions, lamellar layers and the like. The liposomes may be prepared by any of the known methods in the art [Monkkonen, J. et al., 1994, J. Drug Target, 2:299-308; Monkkonen, J. et al., 1993, Calcif. Tissue Int., 53:139-145; Lasic D D., Liposomes Technology Inc., Elsevier, 1993, 63-105. (chapter 3); Winterhalter M, Lasic D D, Chem Phys Lipids, 1993 September; 64(1-3):35-43]. The liposomes may be positively charged, neutral, or, negatively charged.

The liposomes may be a single lipid layer or may be multilamellar. In the case of PS-I as the electron donor, multilamellar vesicles may be advantageous. Alternatively, it may advantageous to increase the surface area of the liposome and adsorb the PS-I on the surface thereof. An exemplary liposomal system for the polypeptides of the present invention includes PS-I constructed within the lipid bilayer, and the fusion protein of the present invention constructed in the enclosed volume as illustrated in FIGS. 2A-B. Surfactant peptide micelles are also contemplated.

In another embodiment, the PSI and fusion protein of the present invention are embedded in a carrier (i.e., embedding agent) of desired properties. In specific embodiments, the embedding agent (or carrier) is a microparticle, nanoparticle, nanosphere, microsphere, nano-plate, microcapsule, or nano-capsule [M. Donbrow in: Microencapsulation and Nanoparticles in Medicine and Pharmacy, CRC Press, Boca Raton, Fla., 347, 1991]. The term carrier includes both polymeric and non-polymeric preparations. According to a specific embodiment, the embedding agent is a nanoparticle. The polypeptides of the present invention may be embedded in the nanoparticle, dispersed uniformly or non-uniformly in the polymer matrix, adsorbed on the surface, or in combination of any of these forms. Polymers which may be used for fabricating the nanoparticles include, but are not limited to, PLA (polylactic acid), and their copolymers, polyanhydrides, polyalkyl-cyanoacrylates (such as polyisobutylcyanoacrylate), polyethyleneglycols, polyethyleneoxides and their derivatives, chitosan, albumin, gelatin and the like.

It will be appreciated that the fusion protein of the present invention and the electron donor need not be encapsulated. Thus, according to yet another embodiment, the fusion protein and the electron donor of the present invention are free in solution.

Hydrogen gas can be harvested from the system of the present invention by direct or indirect biophotolysis:

Direct biophotolysis has been demonstrated under conditions where the resulting oxygen and hydrogen are flushed from the system using inert gas [Greenbaum 1988, Biophysical Journal 54: 365-368].

Indirect biophotolysis intends to circumvent the oxygen sensitivity of the hydrogenases by temporally separating the hydrogen-producing reactions from the oxygen evolving ones. According to one embodiment plant cells (e.g. algae)

may be grown in open ponds to evolve oxygen and store carbohydrates. The plant cells may then be harvested, and placed in an anaerobic reactor. (For whole plants an anaerobic or a semi-anaerobic environment would be created in greenhouses by flushing nitrogen inside at night only). Induction of expression of the fusion protein of the present invention may then ensue concomitant with the inactivation of Photosystem II. Illumination then oxidizes the stored carbohydrate, lipid, and produces hydrogen, either directly or after an anaerobic dark fermentation [Hallenbeck P C 2002, International Journal of Hydrogen Energy 27: 1185-1193]. Since ideally only hydrogen and carbon dioxide are produced in the photobioreactor, gas handling is simpler and less hazardous.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Cloning, Expression, Purification and Analysis of Hydrogenase-Ferredoxin Recombinant Fusion Proteins Materials and Methods Cloning A clone of ferredoxin (petF) was amplified from *Synechocystis* pcc 6803 genome using the following primers:

```
                                          (SEQ ID NO: 7)
Forward:
ATCTATGGCATCCTATACCG;
and
                                          (SEQ ID NO: 8)
Reverse to plant:
TTATGCGGTGAGCTCTTCTTCTTTGTGGGTTTCAATG
```

In addition the C-terminus of the native cyanobacterial ferredoxin was replaced with the higher plant ferredoxin C-terminus using the "reverse to plant primer—SEQ ID NO: 8".

A HydA1 gene of *Chlamydomonas reinhardtii* was expressed essentially as described in (King et al., 2006, J. Bacterilogy: 2163-2172).

The ferredoxin petF was fused to the C-terminus of the target hydrogenase HydA1 according to the free space available in the PSI ferredoxin binding site of plant PSI utilizing the published structures of PSI, ferredoxin and hydrogenase [Peters et al., 1998, Science, 282, 4 December; Nicolet et al., 1999, Structure 7, 13-23; Asada et al., 2000, Biochim Biophys Acta 1490, 269-78; Ben-Shem et al., 2003, Nature 426, 630-5; Amunts et al., 2007, Nature 447, 58-63].

Different linkers as well as several deletions were prepared using the following primers:

Primary For' (Hyd For'):
gatata CATATGGGCTGG (SEQ ID NO: 9)

Primary Rev' (Fd Rev'):
accaga CTCGAGttatgcggtgagctcttc (SEQ ID NO: 10)

1) HydA1 Cr Fd no linker for construction of SEQ ID NO: 1, a direct fusion of HydA1 C-terminus to petF N-terminus.

(SEQ ID NO: 11)
Hyd-Fd Rev:
GGTATAGGATGCCATTTTTTTTTCATCTTTTTCTTCCAC.

(SEQ ID NO: 12)
Hyd-Fd For:
gtggaagaaaaagatgaaaaaaaaATGGCATCCTATACCG.

2) Hyd A1 Cr Fd short linker for construction of SEQ ID NO: 2, a short linker of four glycine a single serine used to create a fusion of HydA1 C-terminus to petF N-terminus.

(SEQ ID NO: 13)
Hyd-Fd Rev:
ggatccgccgccaccTTTTTTTTCATCTTTTTCTTCCAC.

(SEQ ID NO: 14)
Hyd-Fd For:
ggtggcggcggatccATGGCATCCTATACCG.

3) HydA1 Cr Fd medium linker for construction of SEQ ID NO: 3, a medium linker of two repeat of the short linker (composited from four glycine and a single serine) used to create a fusion of HydA1 C-terminus to petF N-terminus.

(SEQ ID NO: 15)
Hyd-Fd Rev:
ggagccgccgccgccggatcctcctcctccTTTTTTTTCATCTTTTTCTT
CCAC.

(SEQ ID NO: 16)
Hyd-Fd For:
ggaggaggaggatccggcggcggcggctccATGGCATCCTATACCG.

4) Hyd A1 Cr C truncated Fd N truncated no linker for construction of SEQ ID NO: 4, a direct fusion of truncated (11aa were deleted at C-terminus) HydA1 C-terminus to truncated (30aa were deleted at N-terminus) petF N-terminus.

(SEQ ID NO: 17)
Hyd-Fd Rev:
gaggatataggtatcgtccacataatgggtatgcag.

(SEQ ID NO: 18)
Hyd-Fd For:
ctgcatacccattatgtggacgatacctatatcctc.

5) Hyd A1 Cr C truncated Fd no linker for construction of SEQ ID NO: 5, a direct fusion of truncated (11aa were deleted at C-terminus) HydA1 C-terminus to petF N-terminus.

(SEQ ID NO: 19)
Hyd-Fd Rev:
cggtataggatgccatcacataatgggtatgcag.

(SEQ ID NO: 20)
Hyd-Fd For:
ctgcatacccattatgtgatggcatcctataccg.

6) Hyd A1 Cr Fd N truncated no linker for construction of SEQ ID NO: 6, a direct fusion of HydA1 C-terminus to truncated (30aa were deleted at N-terminus) petF N-terminus.

(SEQ ID NO: 21)
Hyd-Fd Rev:
gaggatataggtatcgtcttttttttcatcttttttcTTCCAC.

(SEQ ID NO: 22)
Hyd-Fd For:
gtggaagaaaaagatgaaaaaaaagacgatacctatatcctc.

HydA1 and petF genes were assembled using two PCR steps. In the first PCR, each gene HydA1 and petF were amplified separately with the appropriate primers set, which include overlapping region with the product of each other (at sense primers of petF and at antisense primers of HydA1). In the next step the two products of these PCRs were mixed at 1:1 proportion and amplified in a second PCR reaction using only the edges primer set e.g sense primer of hydA1 and antisense primer of petF. The assembly gene fusion product was introduced into the pETDuet system and transformed together with the HydF+G in pCDFduet as described essentially in (King et al., 2006, J. Bacterilogy: 2163-2172).

Protein Expression

Ferredoxin-hydrogenase fusion proteins were expressed in E. coli. (BL-21 DE3 Rosetta). Essentially, an overnight starter of 5 ml TB+ampicillin (Amp) (100 g/ml) 15 µl+5 streptomycin (Sm) (50 g/ml) was washed twice with fresh media (to remove traces of (β-lactamases). 2 ml of the washed starter was diluted into 100 ml TB and 30 mg (300 µl of 100 mg/ml stock solution) Amp and 5 mg Sm (100 µl of 50 mg/ml stock solution) was added. The bacteria were grown in 250 ml flask for ~2.5 hr at 37° C.; 250 RPM to reach $O.D_{600}$=0.5-0.7. Next, Fe citrate 10 mg/100 ml was added and bacteria were grown for an additional 10 minutes at 37° C.; 250 RPM. Induction was initiated by the addition of IPTG 37.5 mg/100 ml. The bacteria were then aerobically grown for 1 hour at 30° C.; 250 RPM, and then transferred to a 100 ml bottle. Argon gas was added directly into the growing media to create bubbles for an additional 6 hours at 30° C. to maintain anaerobic conditions.

Activity Assay

The activity assay was carried as described (King et al., 2006, J. Bacteriol: 2163-2172) as follows: Activities of hydrogenases alone was measured as the evolution of $H_2$ gas from reduced methyl viologen (MV). Activity assays of whole cells extracts were performed with argon-flushed vials that contained an anaerobically prepared whole-cell extract comprising reaction buffer (50 mM potassium phosphate, pH 7; 10 mM MV; 20 mM sodium dithionite; 6 mM NaOH; 0.2% Triton X-100) and 1 ml of anaerobically grown and induced cells.

The fusion protein was analyzed for the ability to produce hydrogen directly from dithionite as an electron donor using their fused ferredoxin part as the electron mediator replacing the function of the chemical mediator methyl viologen (native hydrogenase can not accept electrons directly from dithionite).

Gas Chromatography

Hydrogen production was measured by gas chromatography using Varian 3600 machine equipped with thermal conductivity detector (TCD) and hydrogen column. Nitrogen was used as a carrier gas.

100 µl of gas sample was injected and the area of the specific Hydrogen peak, eluted ~1.25 minutes post injection was calculated using the area of 5.15% hydrogen standard as reference.

Results

The genes of petF and HydA1 was successfully amplified using the primers and assembled together to form the chimera genes as can be seen in FIG. 5.

Next these Hyd-Fd chimeras were cloned into pETDuet plasmids that contained the HydE structural gene as previously described (King et al., 2006, J. Bacteriol: 2163-2172) which is crucial for recombinant expression of hydrogenases in E. coli. FIGS. 6A-B show the two expression plasmids. FIG. 6A is a map of the pETDuet plasmid which contains the Hyd-Fd chimeric genes between the restriction sites NdeI and XhoI of Multiple cloning site II. In addition, the plasmid contains the HydE structural gene. FIG. 6B is a map of the plasmid CDFduet that contains the coding sequences for the two other structural proteins HydF and HydG, both of which are crucial for the recombinant expression of hydrogenase protein in E. coli.

Following preparation of DNA constructs, the protein expression pattern was tested by Western blot analysis using monoclonal antibodies against the StrepTag II (IBA, Gottingen, Germany) (which in our plasmids is located at the N-terminus of the HydA1 protein or the Hyd-Fd chimera). All beside 6HydFd- SEQ ID NO: 6 (direct linkage of HydA1 and N-terminus truncated petF) were well expressed (FIGS. 7A-B).

The hydrogen generated by the expressed chimeras was tested sequentially. First, the hydrogenase component of each chimera was tested separately using a well-known procedure by which dithionite donates electrons to the chemical electron mediator methyl viologen which feeds electrons directly to hydrogenase as described by (King et al., 2006, J. Bacteriol: 2163-2172). Feredoxin electron mediating ability was tested by elimination of the chemical mediator methyl viologen. Under such conditions, hydrogen production by native hydrogenase is negligible while chimera protein produced at least 50% of full activity with the chemical electron mediator methyl viologen. FIG. 8 illustrates hydrogen generation by three selected chimera.

All the tested chimeras generated at least 4 fold more hydrogen than the native hydrogenase.

What is claimed is:

1. An isolated polypeptide comprising an algal Fe-only hydrogenase attached to an algal ferredoxin, comprising an amino acid sequence as set forth in SEQ ID NOs: 23, 25 or 27.

2. An isolated polynucleotide encoding the polypeptide of claim 1.

3. A cell comprising the isolated polynucleotide of claim 2.

4. The cell of claim 3, being selected from the group consisting of a cyanobacterial cell, an algal cell and a higher plant cell.

5. A method of generating hydrogen, the method comprising combining the polypeptide of claim 1 with an electron donor so as to generate an electron transfer chain, wherein said electron transfer chain is configured such that said electron donor is capable of donating electrons to the polypeptide of claim 1, thereby generating hydrogen.

6. The method of claim 5, wherein the generating hydrogen is effected under anaerobic conditions.

7. The method of claim 5, wherein said electron donor is selected from the group consisting of a biomolecule, a chemical, water, an electrode and a combination of the above.

8. The method of claim 7, wherein said biomolecule comprises Photosystem I (PSI) or rhodopsin.

9. The method of claim 5, further comprising harvesting the hydrogen following the generating.

10. The method of claim 5, wherein said combining is effected in a cell-free system.

11. The method of claim 5, wherein said combining is effected in a cellular system.

12. The method of claim 11, wherein said cellular system is selected from the group consisting of a cyanobacteria, an algae and a higher plant.

13. The method of claim 11, further comprising down-regulating an expression of endogenous ferredoxin in said cellular system.

14. The isolated polynucleotide of claim 2, comprising a nucleic acid sequence as set forth in SEQ ID NOs: 1, 3 or 5.

* * * * *

SEQUENCE LISTING

<160> NUMBER OF SEQ ID NOS: 28

<210> SEQ ID NO 1
<211> LENGTH: 1677
<212> TYPE: DNA
<213> ORGANISM: Artificial sequence
<220> FEATURE:
<223> OTHER INFORMATION: pETDuet Hyd E + A Cr Fd with no linker

<400> SEQUENCE: 1

```
atgggctgga gccatccgca gtttgaaaaa agatctgaaa acctgtattt tcagggcgct      60
gctcctgctg ctgaagcgcc gctgagccat gtgcagcagg cgctggcgga actggcgaaa     120
ccgaaagatg atccgacccg taagcatgtg tgcgtgcagg tggcgccggc ggtgcgtgtg     180
gcgatcgcgg aaaccctggg cctggcgccg ggcgcgacca ccccgaaaca gctggcggaa     240
ggcctgcgtc gtctgggctt tgatgaagtg ttcgataccc tgtttggcgc ggatctgacc     300
atcatggaag aaggcagcga actgctgcat cgtctgaccg aacatctgga agcgcatccg     360
catagcgatg aaccgctgcc gatgtttacc agctgctgcc cgggctggat tgcgatgctg     420
gaaaaaagct atccggatct gattccgtat gtgagcagct gcaaaagccc gcagatgatg     480
ctggcggcga tggtgaaaag ctatctggcg gaaaaaaaag gcattgcgcc gaaagatatg     540
gtgatggtga gcattatgcc gtgcacccgt aaacagagcg aagcggatcg tgattggttc     600
tgcgtggatg cggatccgac cctgcgtcag ctggatcatg tgattaccac cgtggaactg     660
ggcaacattt taaagaacg tggcattaac ctggcggaac tgccggaagg cgaatgggat     720
aacccgatgg gcgtgggcag cggcgcgggc gtgctgttcg gcaccaccgg cggcgtgatg     780
gaagcggcgc tgcgtaccgc gtatgaactg tttaccggca ccccgctgcc gcgtctgagc     840
ctgagcgagg tgcgtggcat ggatggcatt aaagagacca acattaccat ggtgccggcg     900
ccgggcagca aatttgaaga actgctgaaa catcgtgcgg cggcgcgtgc ggaagcggcg     960
gcgcatggca cccggggccc gctggcgtgg gatgcggcg cgggctttac cagcgaagat    1020
ggccgtggcg gcattaccct gcgtgtggcg gtggcgaacg gcctgggcaa cgcgaaaaaa    1080
ctgattacca aaatgcaggc gggcgaagcg aaatatgatt ttgtggaaat tatggcgtgc    1140
ccggcgggct gcgtgggcgg cggcggccag ccgcgtagca ccgataaagc gatcacccag    1200
aaacgtcagg cggcgctgta aacctggat gagaagagca ccctgcgtcg tagccatgag    1260
```

```
aacccgagca ttcgtgaact gtatgatacc tatctgggcg aaccgctggg ccataaagcg    1320
catgaactgc tgcatacccca ttatgtggcg ggcggcgtgg aagaaaaaga tgaaaaaaaa   1380
atggcatcct ataccgttaa attgatcacc cccgatggtg aaagttccat cgaatgctct    1440
gacgatacct atatcctcga tgctgcgaa gaagctggcc tagacctgcc ctattcctgc    1500
cgtgctgggg cttgctccac ctgtgccggt aagatcaccg ctggtagtgt tgaccaatcc   1560
gatcagtctt tcttggatga tgaccaaatt gaagctggtt atgttttgac ctgtgtagct    1620
tatcccacct ccgattgcac cattgaaacc cacaaagaag aagagctcac cgcataa       1677
```

<210> SEQ ID NO 2
<211> LENGTH: 1691
<212> TYPE: DNA
<213> ORGANISM: Artificial sequence
<220> FEATURE:
<223> OTHER INFORMATION: pETDuet Hyd E + A Cr Fd with a short linker

<400> SEQUENCE: 2

```
atgggctgga gccatccgca gtttgaaaaa agatctgaaa acctgtattt tcagggcgct    60
gctcctgctg ctgaagcgcc gctgagccat gtgcagcagg cgctggcgga actggcgaaa   120
ccgaaagatg atccgacccg taagcatgtt gcgtgcaggt ggcgccggcg gtgcgtgtgg    180
cgatcgcgga aaccctgggc ctggcgccgg gcgcgaccac cccgaaacag ctggcggaag   240
gcctgcgtcg tctgggcttt gatgaagtgt tcgataccct gtttggcgcg atctgacca    300 tcatggaaga aggcagcgaa ctgctgcatc gtctgaccga acatctggaa gcgcatccgc   360
atagcgatga accgctgccg atgtttacca gctgctgccc gggctggatt gcgatgctgg    420
aaaaaagcta tccggatctg attccgtatg tgagcagctg caaagccccg cagatgatgc   480
tggcggcgat ggtgaaaagc tatctggcgg aaaaaaaagg cattgcgccg aaagatatgg   540
tgatggtgag cattatgccg tgcacccgta acagagcga agcggatcgt gattggttct    600
gcgtggatgc ggatccgacc ctgcgtcagc tggatcatgt gattaccacc gtggaactgg    660
gcaacatttt taaagaacgt ggcattaacc tggcggaact gccggaaggc gaatgggata    720
acccgatggg cgtgggcagc ggcgcggggcg tgctgttcgg caccaccggc ggcgtgatgg   780
aagcggcgct gcgtaccgcg tatgaactgt ttaccggcac cccgctgccg cgtctgagcc    840
tgagcgaggt gcgtggcatg gatggcatta aagagaccaa cattaccatg gtgccggcgc   900
cgggcagcaa atttgaagaa ctgctgaaac atcgtgcggc ggcgcgtgcg aagcggcgg    960 cgcatggcac cccgggcccg ctggcgtggg atggcggcgc gggctttacc agcgaagatg   1020
gccgtggcgg cattaccctg cgtgtggcgg tggcgaacgg cctgggcaac gcgaaaaaac   1080
tgattaccaa aatgcaggcg ggcgaagcga aatatgattt tgtggaaatt atggcgtgcc   1140
cggcgggctg cgtgggcggc ggcggccagc cgcgtagcac cgataaagcg atcacccaga   1200
aacgtcaggc ggcgctgtat aacctggatg agaagagcac cctgcgtcgt agccatgaga   1260
acccgagcat tcgtgaactg tatgatacct atctgggcga accgctgggc cataaagcgc   1320
atgaactgct gcatacccat tatgtggcgg gcggcgtgga agaaaagat gaaaaaaag    1380 gtggcggcgg atccatggca tcctataccg ttaaattgat caccccgat ggtgaaagtt   1440 ccatcgaatg ctctgacgat acctatatcc tcgatgctgc ggaagaagct ggcctagacc   1500
tgccctattc ctgccgtgct ggggcttgct ccacctgtgc cggtaagatc accgctggta    1560
gtgttgacca atccgatcag tctttcttgg atgatgacca aattgaagct ggttatgttt   1620
```

```
tgacctgtgt agcttatccc acctccgatt gcaccattga aacccacaaa gaagaagagc    1680
tcaccgcata a                                                         1691
```

<210> SEQ ID NO 3
<211> LENGTH: 1707
<212> TYPE: DNA
<213> ORGANISM: Artificial sequence
<220> FEATURE:
<223> OTHER INFORMATION: pETDuet Hyd E + A Cr Fd with a medium linker

<400> SEQUENCE: 3

```
atgggctgga gccatccgca gtttgaaaaa agatctgaaa acctgtatttt tcagggcgct     60 gctcctgctg ctgaagcgcc gctgagccat gtgcagcagg cgctggcgga actggcgaaa    120
ccgaaagatg atccgacccg taagcatgtg tgcgtgcagg tggcgccggc ggtgcgtgtg    180
gcgatcgcgg aaaccctggg cctggcgccg ggcgcgacca ccccgaaaca gctggcggaa    240
ggcctgcgtc gtctgggctt tgatgaagtg ttcgataccc gtttggcgc ggatctgacc     300 atcatggaag aaggcagcga actgctgcat cgtctgaccg aacatctgga agcgcatccg    360
catagcgatg aaccgctgcc gatgtttacc agctgctgcc cgggctggat tgcgatgctg    420
gaaaaaagct atccggatct gattccgtat gtgagcagct gcaaaagccc gcagatgatg    480
ctggcggcga tggtgaaaag ctatctggcg aaaaaaaag gcattgcgcc gaaagatatg    540
gtgatggtga gcattatgcc gtgcacccgt aaacagagcg aagcggatcg tgattggttc    600
tgcgtggatg cggatccgac cctgcgtcag ctggatcatg tgattaccac cgtggaactg    660
ggcaacattt taaagaacg tggcattaac ctggcggaaa ctgccggaagg cgaatgggat    720 aacccgatgg gcgtgggcag cggcgcgggc gtgctgttcg gcaccaccgg cggcgtgatg    780
gaagcggcgc tgcgtaccgc gtatgaactg tttaccggca ccccgctgcc gcgtctgagc    840
ctgagcgagg tgcgtggcat ggatggcatt aaagagacca acattaccat ggtgccggcg    900
ccgggcagca aatttgaaga actgctgaaa catcgtgcgg cggcgcgtgc ggaagcggcg    960
gcgcatggca ccccgggccc gctggcgtgg gatggcggcg cgggctttac cagcgaagat   1020
ggccgtggcg gcattaccct gcgtgtggcg gtggcgaacg gcctgggcaa cgcgaaaaaa   1080
ctgattacca aaatgcaggc gggcgaagcg aaatatgatt ttgtggaaat tatggcgtgc   1140
ccggcgggct gcgtgggcgg cggcggccag ccgcgtagca ccgataaagc gatcacccag   1200
aaacgtcagg cggcgctgta acctggat gagaagagca ccctgcgtcg tagccatgag    1260
aacccgagca ttcgtgaact gtatgatacc tatctgggcg aaccgctggg ccataaagcg   1320
catgaactgc tgcataccca ttatgtggcg ggcggcgtgg aagaaaaaga tgaaaaaaaa   1380
ggaggaggag gatccggcgg cggcggctcc atggcatcct ataccgttaa attgatcacc   1440
cccgatggtg aaagttccat cgaatgctct gacgatacct atatcctcga tgctgcggaa   1500
gaagctggcc tagacctgcc ctattcctgc cgtgctgggg cttgctccac ctgtgccggt   1560
aagatcaccg ctggtagtgt tgaccaatcc gatcagtctt tcttggatga tgaccaaatt   1620
gaagctggtt atgttttgac ctgtgtagct tatcccacct ccgattgcac cattgaaacc   1680
cacaaagaag aagagctcac cgcataa                                       1707
```

<210> SEQ ID NO 4
<211> LENGTH: 1584
<212> TYPE: DNA
<213> ORGANISM: Artificial sequence
<220> FEATURE:
<223> OTHER INFORMATION: pETDuet Hyd E + A Cr C' truncated Fd N' truncated and with no linker

<400> SEQUENCE: 4

```
atgggctgga gccatccgca gtttgaaaaa agatctgaaa acctgtattt tcagggcgct    60
gctcctgctg ctgaagcgcc gctgagccat gtgcagcagg cgctggcgga actggcgaaa   120
ccgaaagatg atccgacccg taagcatgtg tgcgtgcagg tggcgccggc ggtgcgtgtg   180
gcgatcgcgg aaaccctggg cctggcgccg ggcgcgacca ccccgaaaca gctggcggaa   240
ggcctgcgtc gtctgggctt tgatgaagtg ttcgataccc tgtttggcgc ggatctgacc   300
atcatggaag aaggcagcga actgctgcat cgtctgaccg aacatctgga agcgcatccg   360
catagcgatg aaccgctgcc gatgtttacc agctgctgcc cgggctggat tgcgatgctg   420
gaaaaaagct atccggatct gattccgtat gtgagcagct gcaaaagccc gcagatgatg   480
ctggcggcga tggtgaaaag ctatctggcg aaaaaaaag gcattgcgcc gaaagatatg   540
gtgatggtga gcattatgcc gtgcacccgt aaacagagcg aagcggatcg tgattggttc   600
tgcgtggatg cggatccgac cctgcgtcag ctggatcatg tgattaccac cgtggaactg   660
ggcaacattt ttaaagaacg tggcattaac ctggcggaac tgccggaagg cgaatgggat   720
aacccgatgg gcgtgggcag cggcgcgggc gtgctgttcg gcaccaccgg cggcgtgatg   780
gaagcggcgc tgcgtaccgc gtatgaactg tttaccggca ccccgctgcc gcgtctgagc   840
ctgagcgagg tgcgtggcat ggatggcatt aaagagacca acattaccat ggtgccggcg   900
ccgggcagca aatttgaaga actgctgaaa catcgtgcgg cggcgcgtgc ggaagcggcg   960
gcgcatggca ccccgggccc gctggcgtgg gatggcggcg cgggctttac cagcgaagat  1020
ggccgtggcg gcattaccct gcgtgtggcg gtggcgaacg gcctgggcaa cgcgaaaaaa  1080
ctgattacca aaatgcaggc gggcgaagcg aaatatgatt ttgtggaaat tatgcgcgtgc  1140
ccggcgggct gcgtgggcgg cggcggccag ccgcgtagca ccgataaagc gatcacccag  1200
aaacgtcagg cggcgctgta taacctggat gagaagagcc cctgcgtcg tagccatgag  1260
aaccccgagca ttcgtgaact gtatgatacc tatctgggcg aaccgctggg ccataaagcg  1320
catgaactgc tgcatacccca ttatgtggac gataccctata tcctcgatgc tgcggaagaa  1380
gctggcctag acctgcccta ttcctgccgt gctggggctt gctccacctg tgccggtaag  1440
atcaccgctg gtagtgttga ccaatccgat cagtctttct tggatgatga ccaaattgaa  1500
gctggttatg tttttgacctg tgtagcttat cccaccctccg attgcaccat tgaaacccac  1560
aaagaagaag agctcaccgc ataa                                          1584
```

<210> SEQ ID NO 5
<211> LENGTH: 1644
<212> TYPE: DNA
<213> ORGANISM: Artificial sequence
<220> FEATURE:
<223> OTHER INFORMATION: pETDuet Hyd E + A Cr C' truncated Fd with no linker

<400> SEQUENCE: 5

```
atgggctgga gccatccgca gtttgaaaaa agatctgaaa acctgtattt tcagggcgct    60
gctcctgctg ctgaagcgcc gctgagccat gtgcagcagg cgctggcgga actggcgaaa   120
ccgaaagatg atccgacccg taagcatgtg tgcgtgcagg tggcgccggc ggtgcgtgtg   180
gcgatcgcgg aaaccctggg cctggcgccg ggcgcgacca ccccgaaaca gctggcggaa   240
ggcctgcgtc gtctgggctt tgatgaagtg ttcgataccc tgtttggcgc ggatctgacc   300
```

-continued

| | |
|---|---|
| atcatggaag aaggcagcga actgctgcat cgtctgaccg aacatctgga agcgcatccg | 360 |
| catagcgatg aaccgctgcc gatgtttacc agctgctgcc cgggctggat tgcgatgctg | 420 |
| gaaaaaagct atccggatct gattccgtat gtgagcagct gcaaaagccc gcagatgatg | 480 |
| ctggcggcga tggtgaaaag ctatctggcg aaaaaaaag gcattgcgcc gaaagatatg | 540 |
| gtgatggtga gcattatgcc gtgcacccgt aaacagagcg aagcggatcg tgattggttc | 600 |
| tgcgtggatg cggatccgac cctgcgtcag ctggatcatg tgattaccac cgtgaactg | 660 |
| ggcaacattt ttaaagaacg tggcattaac ctggcggaac tgccggaagg cgaatgggat | 720 |
| aacccgatgg gcgtgggcag cggcgcgggc gtgctgttcg cgaccaccgg cggcgtgatg | 780 |
| gaagcggcgc tgcgtaccgc gtatgaactg tttaccggca ccccgctgcc gcgtctgagc | 840 |
| ctgagcgagg tgcgtggcat ggatggcatt aaagagacca acattaccat ggtgccggcg | 900 |
| ccgggcagca aatttgaaga actgctgaaa catcgtgcgg cggcgcgtgc ggaagcggcg | 960 |
| gcgcatggca ccccgggccc gctggcgtgg atggcggcg cgggctttac cagcgaagat | 1020 |
| ggccgtggcg gcattaccct gcgtgtggcg gtggcgaacg gctgggcaa cgcgaaaaaa | 1080 |
| ctgattacca aaatgcaggc gggcgaagca aaatatgatt ttgtggaaat tatggcgtgc | 1140 |
| ccggcgggct gcgtgggcgg cggcggccag ccgcgtagca ccgataaagc gatcacccag | 1200 |
| aaacgtcagg cggcgctgta acctggat gagaagagca ccctgcgtcg tagccatgag | 1260 |
| aacccgagca ttcgtgaact gtatgatacc tatctgggcg aaccgctggg ccataaagcg | 1320 |
| catgaactgc tgcataccca ttatgtgatg gcatcctata ccgttaaatt gatcaccccc | 1380 |
| gatggtgaaa gttccatcga atgctctgac gataccctata tcctcgatgc tgcggaagaa | 1440 |
| gctggcctag acctgcccta ttcctgccgt gctggggctt gctccacctg tgccggtaag | 1500 |
| atcaccgctg gtagtgttga ccaatccgat cagtctttct ggatgatga ccaaattgaa | 1560 |
| gctggttatg ttttgacctg tgtagcttat cccacctccg attgcaccat tgaaacccac | 1620 |
| aaagaagaag agctcaccgc ataa | 1644 |

<210> SEQ ID NO 6
<211> LENGTH: 1617
<212> TYPE: DNA
<213> ORGANISM: Artificial sequence
<220> FEATURE:
<223> OTHER INFORMATION: pETDuet Hyd E + A Cr Fd N' truncated

<400> SEQUENCE: 6

| | |
|---|---|
| atgggctgga gccatccgca gtttgaaaaa agatctgaaa acctgtatt tcagggcgct | 60 |
| gctcctgctg ctgaagcgcc gctgagccat gtgcagcagg cgctggcgga actggcgaaa | 120 |
| ccgaaagatg atccgacccg taagcatgtg tgcgtgcagg tggcgccggc ggtgcgtgtg | 180 |
| gcgatcgcgg aaaccctggg cctggcgccg ggcgcgacca ccccgaaaca gctggcggaa | 240 |
| ggcctgcgtc gtctgggctt tgatgaagtg ttcgataccc tgtttggcgc ggatctgacc | 300 |
| atcatggaag aaggcagcga actgctgcat cgtctgaccg aacatctgga agcgcatccg | 360 |
| catagcgatg aaccgctgcc gatgtttacc agctgctgcc cgggctggat tgcgatgctg | 420 |
| gaaaaaagct atccggatct gattccgtat gtgagcagct gcaaaagccc gcagatgatg | 480 |
| ctggcggcga tggtgaaaag ctatctggcg aaaaaaaag gcattgcgcc gaaagatatg | 540 |
| gtgatggtga gcattatgcc gtgcacccgt aaacagagcg aagcggatcg tgattggttc | 600 |
| tgcgtggatg cggatccgac cctgcgtcag ctggatcatg tgattaccac cgtgaactg | 660 |
| ggcaacattt ttaaagaacg tggcattaac ctggcggaac tgccggaagg cgaatgggat | 720 |

```
aacccgatgg gcgtgggcag cggcgcgggc gtgctgttcg gcaccaccgg cggcgtgatg      780
gaagcggcgc tgcgtaccgc gtatgaactg tttaccggca ccccgctgcc gcgtctgagc      840
ctgagcgagg tgcgtggcat ggatggcatt aaagagacca acattaccat ggtgccggcg      900
ccgggcagca aatttgaaga actgctgaaa catcgtgcgg cggcgcgtgc ggaagcggcg      960
gcgcatggca ccccgggccc gctggcgtgg gatggcggcg cgggctttac cagcgaagat     1020
ggccgtggcg gcattaccct gcgtgtggcg gtggcgaacg gcctgggcaa cgcgaaaaaa     1080
ctgattacca aaatgcaggc gggcgaagcg aaatatgatt ttgtggaaat tatggcgtgc     1140
ccggcgggct gcgtgggcgg cggcggccag ccgcgtagca ccgataaagc gatcacccag     1200
aaacgtcagg cggcgctgta aacctggat gagaagagca ccctgcgtcg tagccatgag      1260
aacccgagca ttcgtgaact gtatgatacc tatctgggcg aaccgctggg ccataaagcg     1320
catgaactgc tgcataccca ttatgtggcg ggcggcgtgg aagaaaaaga tgaaaaaaaa     1380
gacgatacct atatcctcga tgctgcggaa gaagctggcc tagacctgcc ctattcctgc     1440
cgtgctgggg cttgctccac ctgtgccggt aagatcaccg ctggtagtgt tgaccaatcc     1500
gatcagtctt tcttggatga tgaccaaatt gaagctggtt atgttttgac ctgtgtagct     1560
tatcccacct ccgattgcac cattgaaacc cacaaagaag aagagctcac cgcataa       1617

<210> SEQ ID NO 7
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 7
atctatggca tcctataccg                                                   20

<210> SEQ ID NO 8
<211> LENGTH: 37
<212> TYPE: DNA
<213> ORGANISM: Artificial sequence
<220> FEATURE:
<223> OTHER INFORMATION: Single strand DNA oligonucleotide

<400> SEQUENCE: 8
ttatgcggtg agctcttctt ctttgtgggt ttcaatg                                37

<210> SEQ ID NO 9
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 9
gatatacata tgggctgg                                                     18

<210> SEQ ID NO 10
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 10
accagactcg agttatgcgg tgagctcttc                                        30
```

<210> SEQ ID NO 11
<211> LENGTH: 39
<212> TYPE: DNA
<213> ORGANISM: Artificial sequence
<220> FEATURE:
<223> OTHER INFORMATION: Single strand DNA oligonucleotide

<400> SEQUENCE: 11
ggtataggat gccattttt tttcatcttt ttcttccac                          39

<210> SEQ ID NO 12
<211> LENGTH: 40
<212> TYPE: DNA
<213> ORGANISM: Artificial sequence
<220> FEATURE:
<223> OTHER INFORMATION: Single strand DNA oligonucleotide

<400> SEQUENCE: 12
gtggaagaaa aagatgaaaa aaaaatggca tcctataccg                        40

<210> SEQ ID NO 13
<211> LENGTH: 39
<212> TYPE: DNA
<213> ORGANISM: Artificial sequence
<220> FEATURE:
<223> OTHER INFORMATION: Single strand DNA oligonucleotide

<400> SEQUENCE: 13
ggatccgccg ccaccttttt tttcatcttt ttcttccac                         39

<210> SEQ ID NO 14
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 14
ggtggcggcg gatccatggc atcctatacc g                                 31

<210> SEQ ID NO 15
<211> LENGTH: 54
<212> TYPE: DNA
<213> ORGANISM: Artificial sequence
<220> FEATURE:
<223> OTHER INFORMATION: Single strand DNA oligonucleotide

<400> SEQUENCE: 15
ggagccgccg ccgccggatc ctcctcctcc tttttttca tctttttctt ccac         54

<210> SEQ ID NO 16
<211> LENGTH: 46
<212> TYPE: DNA
<213> ORGANISM: Artificial sequence
<220> FEATURE:
<223> OTHER INFORMATION: Single strand DNA oligonucleotide

<400> SEQUENCE: 16
ggaggaggag gatccggcgg cggcggctcc atggcatcct ataccg                 46

<210> SEQ ID NO 17
<211> LENGTH: 36
<212> TYPE: DNA
<213> ORGANISM: Artificial sequence
<220> FEATURE:
<223> OTHER INFORMATION: Single strand DNA oligonucleotide

<400> SEQUENCE: 17
gaggatatag gtatcgtcca cataatgggt atgcag                                   36

<210> SEQ ID NO 18
<211> LENGTH: 36
<212> TYPE: DNA
<213> ORGANISM: Artificial sequence
<220> FEATURE:
<223> OTHER INFORMATION: Single strand DNA oligonucleotide

<400> SEQUENCE: 18
ctgcataccc attatgtgga cgatacctat atcctc                                   36

<210> SEQ ID NO 19
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 19
cggtatagga tgccatcaca taatgggtat gcag                                     34

<210> SEQ ID NO 20
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 20
ctgcataccc attatgtgat ggcatcctat accg                                     34

<210> SEQ ID NO 21
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 21
gaggatatag gtatcgtctt tttttcatc tttttcttcc ac                             42

<210> SEQ ID NO 22
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 22
gtggaagaaa aagatgaaaa aaaagacgat acctatatcc tc                            42

<210> SEQ ID NO 23
<211> LENGTH: 558
<212> TYPE: PRT
<213> ORGANISM: Artificial sequence
<220> FEATURE:
<223> OTHER INFORMATION: 1HydFd : a recombinant product of pETDuet Hyd
      E + A Cr Fd with no linker

<400> SEQUENCE: 23

Met Gly Trp Ser His Pro Gln Phe Glu Lys Arg Ser Glu Asn Leu Tyr
1               5                   10                  15

-continued

```
Phe Gln Gly Ala Ala Pro Ala Glu Ala Pro Leu Ser His Val Gln
         20                  25                  30
Gln Ala Leu Ala Glu Leu Ala Lys Pro Lys Asp Asp Pro Thr Arg Lys
             35                  40                  45
His Val Cys Val Gln Val Ala Pro Ala Val Arg Val Ala Ile Ala Glu
         50                  55                  60
Thr Leu Gly Leu Ala Pro Gly Ala Thr Thr Pro Lys Gln Leu Ala Glu
 65                  70                  75                  80
Gly Leu Arg Arg Leu Gly Phe Asp Glu Val Phe Asp Thr Leu Phe Gly
                 85                  90                  95
Ala Asp Leu Thr Ile Met Glu Glu Gly Ser Glu Leu Leu His Arg Leu
            100                 105                 110
Thr Glu His Leu Glu Ala His Pro His Ser Asp Glu Pro Leu Pro Met
        115                 120                 125
Phe Thr Ser Cys Cys Pro Gly Trp Ile Ala Met Leu Glu Lys Ser Tyr
130                 135                 140
Pro Asp Leu Ile Pro Tyr Val Ser Ser Cys Lys Ser Pro Gln Met Met
145                 150                 155                 160
Leu Ala Ala Met Val Lys Ser Tyr Leu Ala Glu Lys Lys Gly Ile Ala
                165                 170                 175
Pro Lys Asp Met Val Met Val Ser Ile Met Pro Cys Thr Arg Lys Gln
            180                 185                 190
Ser Glu Ala Asp Arg Asp Trp Phe Cys Val Asp Ala Asp Pro Thr Leu
        195                 200                 205
Arg Gln Leu Asp His Val Ile Thr Thr Val Glu Leu Gly Asn Ile Phe
210                 215                 220
Lys Glu Arg Gly Ile Asn Leu Ala Glu Leu Pro Glu Gly Glu Trp Asp
225                 230                 235                 240
Asn Pro Met Gly Val Gly Ser Gly Ala Gly Val Leu Phe Gly Thr Thr
                245                 250                 255
Gly Gly Val Met Glu Ala Ala Leu Arg Thr Ala Tyr Glu Leu Phe Thr
            260                 265                 270
Gly Thr Pro Leu Pro Arg Leu Ser Leu Ser Glu Val Arg Gly Met Asp
        275                 280                 285
Gly Ile Lys Glu Thr Asn Ile Thr Met Val Pro Ala Pro Gly Ser Lys
290                 295                 300
Phe Glu Glu Leu Leu Lys His Arg Ala Ala Arg Ala Glu Ala Ala
305                 310                 315                 320
Ala His Gly Thr Pro Gly Pro Leu Ala Trp Asp Gly Gly Ala Gly Phe
                325                 330                 335
Thr Ser Glu Asp Gly Arg Gly Gly Ile Thr Leu Arg Val Ala Val Ala
            340                 345                 350
Asn Gly Leu Gly Asn Ala Lys Lys Leu Ile Thr Lys Met Gln Ala Gly
        355                 360                 365
Glu Ala Lys Tyr Asp Phe Val Glu Ile Met Ala Cys Pro Ala Gly Cys
370                 375                 380
Val Gly Gly Gly Gln Pro Arg Ser Thr Lys Ala Ile Thr Gln
385                 390                 395                 400
Lys Arg Gln Ala Ala Leu Tyr Asn Leu Asp Glu Lys Ser Thr Leu Arg
                405                 410                 415
Arg Ser His Glu Asn Pro Ser Ile Arg Glu Leu Tyr Asp Thr Tyr Leu
            420                 425                 430
Gly Glu Pro Leu Gly His Lys Ala His Glu Leu Leu His Thr His Tyr
```

```
              435                 440                 445
Val Ala Gly Gly Val Glu Glu Lys Asp Glu Lys Lys Met Ala Ser Tyr
        450                 455                 460

Thr Val Lys Leu Ile Thr Pro Asp Gly Glu Ser Ser Ile Glu Cys Ser
465                 470                 475                 480

Asp Asp Thr Tyr Ile Leu Asp Ala Ala Glu Ala Gly Leu Asp Leu
                    485                 490                 495

Pro Tyr Ser Cys Arg Ala Gly Ala Cys Ser Thr Cys Ala Gly Lys Ile
                500                 505                 510

Thr Ala Gly Ser Val Asp Gln Ser Asp Gln Ser Phe Leu Asp Asp Asp
            515                 520                 525

Gln Ile Glu Ala Gly Tyr Val Leu Thr Cys Val Ala Tyr Pro Thr Ser
        530                 535                 540

Asp Cys Thr Ile Glu Thr His Lys Glu Glu Leu Thr Ala
545                 550                 555

<210> SEQ ID NO 24
<211> LENGTH: 563
<212> TYPE: PRT
<213> ORGANISM: Artificial sequence
<220> FEATURE:
<223> OTHER INFORMATION: 2HydFd : a recombinant product of pETDuet Hyd
      E + A Cr Fd with a short linker

<400> SEQUENCE: 24

Met Gly Trp Ser His Pro Gln Phe Glu Lys Arg Ser Glu Asn Leu Tyr
1               5                   10                  15

Phe Gln Gly Ala Ala Pro Ala Ala Glu Ala Pro Leu Ser His Val Gln
                20                  25                  30

Gln Ala Leu Ala Glu Leu Ala Lys Pro Lys Asp Asp Pro Thr Arg Lys
            35                  40                  45

His Val Cys Val Gln Val Ala Pro Ala Val Arg Val Ala Ile Ala Glu
        50                  55                  60

Thr Leu Gly Leu Ala Pro Gly Ala Thr Thr Pro Lys Gln Leu Ala Glu
65                  70                  75                  80

Gly Leu Arg Arg Leu Gly Phe Asp Glu Val Phe Asp Thr Leu Phe Gly
                85                  90                  95

Ala Asp Leu Thr Ile Met Glu Glu Gly Ser Glu Leu Leu His Arg Leu
                100                 105                 110

Thr Glu His Leu Glu Ala His Pro His Ser Asp Glu Pro Leu Pro Met
            115                 120                 125

Phe Thr Ser Cys Cys Pro Gly Trp Ile Ala Met Leu Glu Lys Ser Tyr
        130                 135                 140

Pro Asp Leu Ile Pro Tyr Val Ser Ser Cys Lys Ser Pro Gln Met Met
145                 150                 155                 160

Leu Ala Ala Met Val Lys Ser Tyr Leu Ala Glu Lys Lys Gly Ile Ala
                165                 170                 175

Pro Lys Asp Met Val Met Val Ser Ile Met Pro Cys Thr Arg Lys Gln
                180                 185                 190

Ser Glu Ala Asp Arg Asp Trp Phe Cys Val Asp Ala Asp Pro Thr Leu
            195                 200                 205

Arg Gln Leu Asp His Val Ile Thr Thr Val Glu Leu Gly Asn Ile Phe
        210                 215                 220

Lys Glu Arg Gly Ile Asn Leu Ala Glu Leu Pro Glu Gly Glu Trp Asp
225                 230                 235                 240
```

```
Asn Pro Met Gly Val Gly Ser Gly Ala Gly Val Leu Phe Gly Thr Thr
                245                 250                 255
Gly Gly Val Met Glu Ala Ala Leu Arg Thr Ala Tyr Glu Leu Phe Thr
            260                 265                 270
Gly Thr Pro Leu Pro Arg Leu Ser Leu Ser Glu Val Arg Gly Met Asp
        275                 280                 285
Gly Ile Lys Glu Thr Asn Ile Thr Met Val Pro Ala Pro Gly Ser Lys
    290                 295                 300
Phe Glu Glu Leu Leu Lys His Arg Ala Ala Arg Ala Glu Ala Ala Ala
305                 310                 315                 320
Ala His Gly Thr Pro Gly Pro Leu Ala Trp Asp Gly Ala Gly Phe
                325                 330                 335
Thr Ser Glu Asp Gly Arg Gly Ile Thr Leu Arg Val Ala Val Ala
            340                 345                 350
Asn Gly Leu Gly Asn Ala Lys Lys Leu Ile Thr Lys Met Gln Ala Gly
        355                 360                 365
Glu Ala Lys Tyr Asp Phe Val Glu Ile Met Ala Cys Pro Ala Gly Cys
    370                 375                 380
Val Gly Gly Gly Gln Pro Arg Ser Thr Asp Lys Ala Ile Thr Gln
385                 390                 395                 400
Lys Arg Gln Ala Ala Leu Tyr Asn Leu Asp Glu Lys Ser Thr Leu Arg
                405                 410                 415
Arg Ser His Glu Asn Pro Ser Ile Arg Glu Leu Tyr Asp Thr Tyr Leu
            420                 425                 430
Gly Glu Pro Leu Gly His Lys Ala His Glu Leu Leu His Thr His Tyr
        435                 440                 445
Val Ala Gly Gly Val Glu Glu Lys Asp Glu Lys Lys Gly Gly Gly Gly
    450                 455                 460
Ser Met Ala Ser Tyr Thr Val Lys Leu Ile Thr Pro Asp Gly Glu Ser
465                 470                 475                 480
Ser Ile Glu Cys Ser Asp Asp Thr Tyr Ile Leu Asp Ala Ala Glu Glu
                485                 490                 495
Ala Gly Leu Asp Leu Pro Tyr Ser Cys Arg Ala Gly Ala Cys Ser Thr
            500                 505                 510
Cys Ala Gly Lys Ile Thr Ala Gly Ser Val Asp Gln Ser Asp Gln Ser
        515                 520                 525
Phe Leu Asp Asp Asp Gln Ile Glu Ala Gly Tyr Val Leu Thr Cys Val
    530                 535                 540
Ala Tyr Pro Thr Ser Asp Cys Thr Ile Glu Thr His Lys Glu Glu Glu
545                 550                 555                 560
Leu Thr Ala

<210> SEQ ID NO 25
<211> LENGTH: 568
<212> TYPE: PRT
<213> ORGANISM: Artificial sequence
<220> FEATURE:
<223> OTHER INFORMATION: 3HydFd : a recombinant product of pETDuet Hyd
      E + A Cr Fd with a medium linker

<400> SEQUENCE: 25

Met Gly Trp Ser His Pro Gln Phe Glu Lys Arg Ser Glu Asn Leu Tyr
1               5                   10                  15
Phe Gln Gly Ala Ala Pro Ala Ala Glu Ala Pro Leu Ser His Val Gln
            20                  25                  30
```

-continued

```
Gln Ala Leu Ala Glu Leu Ala Lys Pro Lys Asp Asp Pro Thr Arg Lys
             35                  40                  45

His Val Cys Val Gln Val Ala Pro Ala Val Arg Val Ala Ile Ala Glu
 50                  55                  60

Thr Leu Gly Leu Ala Pro Gly Ala Thr Thr Pro Lys Gln Leu Ala Glu
 65                  70                  75                  80

Gly Leu Arg Arg Leu Gly Phe Asp Glu Val Phe Asp Thr Leu Phe Gly
                 85                  90                  95

Ala Asp Leu Thr Ile Met Glu Glu Gly Ser Glu Leu Leu His Arg Leu
            100                 105                 110

Thr Glu His Leu Glu Ala His Pro His Ser Asp Glu Pro Leu Pro Met
            115                 120                 125

Phe Thr Ser Cys Cys Pro Gly Trp Ile Ala Met Leu Glu Lys Ser Tyr
            130                 135                 140

Pro Asp Leu Ile Pro Tyr Val Ser Ser Cys Lys Ser Pro Gln Met Met
145                 150                 155                 160

Leu Ala Ala Met Val Lys Ser Tyr Leu Ala Glu Lys Lys Gly Ile Ala
                165                 170                 175

Pro Lys Asp Met Val Met Val Ser Ile Met Pro Cys Thr Arg Lys Gln
            180                 185                 190

Ser Glu Ala Asp Arg Asp Trp Phe Cys Val Asp Ala Asp Pro Thr Leu
            195                 200                 205

Arg Gln Leu Asp His Val Ile Thr Thr Val Glu Leu Gly Asn Ile Phe
            210                 215                 220

Lys Glu Arg Gly Ile Asn Leu Ala Glu Leu Pro Glu Gly Glu Trp Asp
225                 230                 235                 240

Asn Pro Met Gly Val Gly Ser Gly Ala Gly Val Leu Phe Gly Thr Thr
                245                 250                 255

Gly Gly Val Met Glu Ala Ala Leu Arg Thr Ala Tyr Glu Leu Phe Thr
            260                 265                 270

Gly Thr Pro Leu Pro Arg Leu Ser Leu Ser Glu Val Arg Gly Met Asp
            275                 280                 285

Gly Ile Lys Glu Thr Asn Ile Thr Met Val Pro Ala Pro Gly Ser Lys
            290                 295                 300

Phe Glu Glu Leu Leu Lys His Arg Ala Ala Arg Ala Glu Ala Ala
305                 310                 315                 320

Ala His Gly Thr Pro Gly Pro Leu Ala Trp Asp Gly Gly Ala Gly Phe
                325                 330                 335

Thr Ser Glu Asp Gly Arg Gly Ile Thr Leu Arg Val Ala Val Ala
            340                 345                 350

Asn Gly Leu Gly Asn Ala Lys Lys Leu Ile Thr Lys Met Gln Ala Gly
            355                 360                 365

Glu Ala Lys Tyr Asp Phe Val Glu Ile Met Ala Cys Pro Ala Gly Cys
            370                 375                 380

Val Gly Gly Gly Gln Pro Arg Ser Thr Asp Lys Ala Ile Thr Gln
385                 390                 395                 400

Lys Arg Gln Ala Ala Leu Tyr Asn Leu Asp Glu Lys Ser Thr Leu Arg
                405                 410                 415

Arg Ser His Glu Asn Pro Ser Ile Arg Glu Leu Tyr Asp Thr Tyr Leu
            420                 425                 430

Gly Glu Pro Leu Gly His Lys Ala His Glu Leu Leu His Thr His Tyr
            435                 440                 445

Val Ala Gly Gly Val Glu Glu Lys Asp Glu Lys Lys Gly Gly Gly Gly
```

```
                    450                 455                 460
Ser Gly Gly Gly Ser Met Ala Ser Tyr Thr Val Lys Leu Ile Thr
465                 470                 475                 480

Pro Asp Gly Glu Ser Ser Ile Glu Cys Ser Asp Asp Thr Tyr Ile Leu
                485                 490                 495

Asp Ala Ala Glu Glu Ala Gly Leu Asp Leu Pro Tyr Ser Cys Arg Ala
                500                 505                 510

Gly Ala Cys Ser Thr Cys Ala Gly Lys Ile Thr Ala Gly Ser Val Asp
                515                 520                 525

Gln Ser Asp Gln Ser Phe Leu Asp Asp Gln Ile Glu Ala Gly Tyr
530                 535                 540

Val Leu Thr Cys Val Ala Tyr Pro Thr Ser Asp Cys Thr Ile Glu Thr
545                 550                 555                 560

His Lys Glu Glu Glu Leu Thr Ala
                565

<210> SEQ ID NO 26
<211> LENGTH: 527
<212> TYPE: PRT
<213> ORGANISM: Artificial sequence
<220> FEATURE:
<223> OTHER INFORMATION: 4HydFd : a recombinant product of Hyd E + A Cr
      C' truncated Fd N' truncated and with no linker

<400> SEQUENCE: 26

Met Gly Trp Ser His Pro Gln Phe Glu Lys Arg Ser Glu Asn Leu Tyr
1               5                   10                  15

Phe Gln Gly Ala Ala Pro Ala Ala Glu Ala Pro Leu Ser His Val Gln
                20                  25                  30

Gln Ala Leu Ala Glu Leu Ala Lys Pro Lys Asp Asp Pro Thr Arg Lys
            35                  40                  45

His Val Cys Val Gln Val Ala Pro Ala Val Arg Val Ala Ile Ala Glu
        50                  55                  60

Thr Leu Gly Leu Ala Pro Gly Ala Thr Thr Pro Lys Gln Leu Ala Glu
65                  70                  75                  80

Gly Leu Arg Arg Leu Gly Phe Asp Glu Val Phe Asp Thr Leu Phe Gly
                85                  90                  95

Ala Asp Leu Thr Ile Met Glu Glu Gly Ser Glu Leu Leu His Arg Leu
                100                 105                 110

Thr Glu His Leu Glu Ala His Pro His Ser Asp Glu Pro Leu Pro Met
            115                 120                 125

Phe Thr Ser Cys Cys Pro Gly Trp Ile Ala Met Leu Glu Lys Ser Tyr
130                 135                 140

Pro Asp Leu Ile Pro Tyr Val Ser Ser Cys Lys Ser Pro Gln Met Met
145                 150                 155                 160

Leu Ala Ala Met Val Lys Ser Tyr Leu Ala Glu Lys Lys Gly Ile Ala
                165                 170                 175

Pro Lys Asp Met Val Met Val Ser Ile Met Pro Cys Thr Arg Lys Gln
                180                 185                 190

Ser Glu Ala Asp Arg Asp Trp Phe Cys Val Asp Ala Asp Pro Thr Leu
            195                 200                 205

Arg Gln Leu Asp His Val Ile Thr Thr Val Glu Leu Gly Asn Ile Phe
        210                 215                 220

Lys Glu Arg Gly Ile Asn Leu Ala Glu Leu Pro Glu Gly Glu Trp Asp
225                 230                 235                 240
```

```
Asn Pro Met Gly Val Gly Ser Gly Ala Gly Val Leu Phe Gly Thr Thr
            245                 250                 255

Gly Gly Val Met Glu Ala Ala Leu Arg Thr Ala Tyr Glu Leu Phe Thr
        260                 265                 270

Gly Thr Pro Leu Pro Arg Leu Ser Leu Ser Glu Val Arg Gly Met Asp
    275                 280                 285

Gly Ile Lys Glu Thr Asn Ile Thr Met Val Pro Ala Pro Gly Ser Lys
290                 295                 300

Phe Glu Glu Leu Leu Lys His Arg Ala Ala Arg Ala Glu Ala Ala
305                 310                 315                 320

Ala His Gly Thr Pro Gly Pro Leu Ala Trp Asp Gly Ala Gly Phe
        325                 330                 335

Thr Ser Glu Asp Gly Arg Gly Ile Thr Leu Arg Val Ala Val Ala
            340                 345                 350

Asn Gly Leu Gly Asn Ala Lys Lys Leu Ile Thr Lys Met Gln Ala Gly
        355                 360                 365

Glu Ala Lys Tyr Asp Phe Val Glu Ile Met Ala Cys Pro Ala Gly Cys
    370                 375                 380

Val Gly Gly Gly Gln Pro Arg Ser Thr Asp Lys Ala Ile Thr Gln
385                 390                 395                 400

Lys Arg Gln Ala Ala Leu Tyr Asn Leu Asp Glu Lys Ser Thr Leu Arg
                405                 410                 415

Arg Ser His Glu Asn Pro Ser Ile Arg Glu Leu Tyr Asp Thr Tyr Leu
            420                 425                 430

Gly Glu Pro Leu Gly His Lys Ala His Glu Leu Leu His Thr His Tyr
        435                 440                 445

Val Asp Asp Thr Tyr Ile Leu Asp Ala Ala Glu Glu Ala Gly Leu Asp
    450                 455                 460

Leu Pro Tyr Ser Cys Arg Ala Gly Ala Cys Ser Thr Cys Ala Gly Lys
465                 470                 475                 480

Ile Thr Ala Gly Ser Val Asp Gln Ser Asp Gln Ser Phe Leu Asp Asp
                485                 490                 495

Asp Gln Ile Glu Ala Gly Tyr Val Leu Thr Cys Val Ala Tyr Pro Thr
            500                 505                 510

Ser Asp Cys Thr Ile Glu Thr His Lys Glu Glu Glu Leu Thr Ala
        515                 520                 525

<210> SEQ ID NO 27
<211> LENGTH: 547
<212> TYPE: PRT
<213> ORGANISM: Artificial sequence
<220> FEATURE:
<223> OTHER INFORMATION: 5HydFd : a recombinant product of pETDuet Hyd
      E + A Cr C' truncated Fd and with no linker

<400> SEQUENCE: 27

Met Gly Trp Ser His Pro Gln Phe Glu Lys Arg Ser Glu Asn Leu Tyr
1               5                   10                  15

Phe Gln Gly Ala Ala Pro Ala Ala Glu Ala Pro Leu Ser His Val Gln
            20                  25                  30

Gln Ala Leu Ala Glu Leu Ala Lys Pro Lys Asp Asp Pro Thr Arg Lys
        35                  40                  45

His Val Cys Val Gln Val Ala Pro Ala Val Arg Val Ala Ile Ala Glu
    50                  55                  60

Thr Leu Gly Leu Ala Pro Gly Ala Thr Thr Pro Lys Gln Leu Ala Glu
65                  70                  75                  80
```

```
Gly Leu Arg Arg Leu Gly Phe Asp Glu Val Phe Asp Thr Leu Phe Gly
                85                  90                  95

Ala Asp Leu Thr Ile Met Glu Glu Gly Ser Glu Leu Leu His Arg Leu
            100                 105                 110

Thr Glu His Leu Glu Ala His Pro His Ser Asp Glu Pro Leu Pro Met
        115                 120                 125

Phe Thr Ser Cys Cys Pro Gly Trp Ile Ala Met Leu Glu Lys Ser Tyr
130                 135                 140

Pro Asp Leu Ile Pro Tyr Val Ser Ser Cys Lys Ser Pro Gln Met Met
145                 150                 155                 160

Leu Ala Ala Met Val Lys Ser Tyr Leu Ala Glu Lys Lys Gly Ile Ala
                165                 170                 175

Pro Lys Asp Met Val Met Val Ser Ile Met Pro Cys Thr Arg Lys Gln
            180                 185                 190

Ser Glu Ala Asp Arg Asp Trp Phe Cys Val Asp Ala Asp Pro Thr Leu
        195                 200                 205

Arg Gln Leu Asp His Val Ile Thr Val Glu Leu Gly Asn Ile Phe
210                 215                 220

Lys Glu Arg Gly Ile Asn Leu Ala Glu Leu Pro Glu Gly Glu Trp Asp
225                 230                 235                 240

Asn Pro Met Gly Val Gly Ser Gly Ala Gly Val Leu Phe Gly Thr Thr
                245                 250                 255

Gly Gly Val Met Glu Ala Ala Leu Arg Thr Ala Tyr Glu Leu Phe Thr
            260                 265                 270

Gly Thr Pro Leu Pro Arg Leu Ser Leu Ser Glu Val Arg Gly Met Asp
        275                 280                 285

Gly Ile Lys Glu Thr Asn Ile Thr Met Val Pro Ala Pro Gly Ser Lys
290                 295                 300

Phe Glu Glu Leu Leu Lys His Arg Ala Ala Ala Arg Ala Glu Ala Ala
305                 310                 315                 320

Ala His Gly Thr Pro Gly Pro Leu Ala Trp Asp Gly Gly Ala Gly Phe
                325                 330                 335

Thr Ser Glu Asp Gly Arg Gly Gly Ile Thr Leu Arg Val Ala Val Ala
            340                 345                 350

Asn Gly Leu Gly Asn Ala Lys Lys Leu Ile Thr Lys Met Gln Ala Gly
        355                 360                 365

Glu Ala Lys Tyr Asp Phe Val Glu Ile Met Ala Cys Pro Ala Gly Cys
370                 375                 380

Val Gly Gly Gly Gly Gln Pro Arg Ser Thr Asp Lys Ala Ile Thr Gln
385                 390                 395                 400

Lys Arg Gln Ala Ala Leu Tyr Asn Leu Asp Glu Lys Ser Thr Leu Arg
                405                 410                 415

Arg Ser His Glu Asn Pro Ser Ile Arg Glu Leu Tyr Asp Thr Tyr Leu
            420                 425                 430

Gly Glu Pro Leu Gly His Lys Ala His Glu Leu Leu His Thr His Tyr
        435                 440                 445

Val Met Ala Ser Tyr Thr Val Lys Leu Ile Thr Pro Asp Gly Glu Ser
450                 455                 460

Ser Ile Glu Cys Ser Asp Asp Thr Tyr Ile Leu Asp Ala Ala Glu Glu
465                 470                 475                 480

Ala Gly Leu Asp Leu Pro Tyr Ser Cys Arg Ala Gly Ala Cys Ser Thr
                485                 490                 495
```

```
Cys Ala Gly Lys Ile Thr Ala Gly Ser Val Asp Gln Ser Gln Ser
            500                 505                 510

Phe Leu Asp Asp Gln Ile Glu Ala Gly Tyr Val Leu Thr Cys Val
            515                 520                 525

Ala Tyr Pro Thr Ser Asp Cys Thr Ile Glu Thr His Lys Glu Glu
            530                 535                 540

Leu Thr Ala
545

<210> SEQ ID NO 28
<211> LENGTH: 538
<212> TYPE: PRT
<213> ORGANISM: Artificial sequence
<220> FEATURE:
<223> OTHER INFORMATION: 6HydFd : a recombinant product of pETDuet Hyd
      E + A Cr Fd N' truncated

<400> SEQUENCE: 28

Met Gly Trp Ser His Pro Gln Phe Glu Lys Arg Ser Glu Asn Leu Tyr
1               5                   10                  15

Phe Gln Gly Ala Ala Pro Ala Ala Glu Ala Pro Leu Ser His Val Gln
                20                  25                  30

Gln Ala Leu Ala Glu Leu Ala Lys Pro Lys Asp Asp Pro Thr Arg Lys
            35                  40                  45

His Val Cys Val Gln Val Ala Pro Ala Val Arg Val Ala Ile Ala Glu
        50                  55                  60

Thr Leu Gly Leu Ala Pro Gly Ala Thr Thr Pro Lys Gln Leu Ala Glu
65                  70                  75                  80

Gly Leu Arg Arg Leu Gly Phe Asp Glu Val Phe Asp Thr Leu Phe Gly
                85                  90                  95

Ala Asp Leu Thr Ile Met Glu Glu Gly Ser Leu Leu His Arg Leu
            100                 105                 110

Thr Glu His Leu Glu Ala His Pro His Ser Asp Glu Pro Leu Pro Met
        115                 120                 125

Phe Thr Ser Cys Cys Pro Gly Trp Ile Ala Met Leu Glu Lys Ser Tyr
    130                 135                 140

Pro Asp Leu Ile Pro Tyr Val Ser Ser Cys Lys Ser Pro Gln Met Met
145                 150                 155                 160

Leu Ala Ala Met Val Lys Ser Tyr Leu Ala Glu Lys Lys Gly Ile Ala
                165                 170                 175

Pro Lys Asp Met Val Met Val Ser Ile Met Pro Cys Thr Arg Lys Gln
            180                 185                 190

Ser Glu Ala Asp Arg Asp Trp Phe Cys Val Asp Ala Asp Pro Thr Leu
        195                 200                 205

Arg Gln Leu Asp His Val Ile Thr Thr Val Glu Leu Gly Asn Ile Phe
    210                 215                 220

Lys Glu Arg Gly Ile Asn Leu Ala Glu Leu Pro Glu Gly Glu Trp Asp
225                 230                 235                 240

Asn Pro Met Gly Val Gly Ser Gly Ala Gly Val Leu Phe Gly Thr Thr
                245                 250                 255

Gly Gly Val Met Glu Ala Ala Leu Arg Thr Ala Tyr Gly Leu Phe Thr
            260                 265                 270

Gly Thr Pro Leu Pro Arg Leu Ser Leu Ser Glu Val Arg Gly Met Asp
        275                 280                 285

Gly Ile Lys Glu Thr Asn Ile Thr Met Val Pro Ala Pro Gly Ser Lys
    290                 295                 300
```

-continued

```
Phe Glu Glu Leu Leu Lys His Arg Ala Ala Ala Arg Ala Glu Ala Ala
305                 310                 315                 320

Ala His Gly Thr Pro Gly Pro Leu Ala Trp Asp Gly Gly Ala Gly Phe
            325                 330                 335

Thr Ser Glu Asp Gly Arg Gly Gly Ile Thr Leu Arg Val Ala Val Ala
            340                 345                 350

Asn Gly Leu Gly Asn Ala Lys Lys Leu Ile Thr Lys Met Gln Ala Gly
        355                 360                 365

Glu Ala Lys Tyr Asp Phe Val Glu Ile Met Ala Cys Pro Ala Gly Cys
    370                 375                 380

Val Gly Gly Gly Gln Pro Arg Ser Thr Asp Lys Ala Ile Thr Gln
385                 390                 395                 400

Lys Arg Gln Ala Ala Leu Tyr Asn Leu Asp Glu Lys Ser Thr Leu Arg
            405                 410                 415

Arg Ser His Glu Asn Pro Ser Ile Arg Glu Leu Tyr Asp Thr Tyr Leu
            420                 425                 430

Gly Glu Pro Leu Gly His Lys Ala His Glu Leu Leu His Thr His Tyr
            435                 440                 445

Val Ala Gly Gly Val Glu Glu Lys Asp Glu Lys Lys Asp Asp Thr Tyr
    450                 455                 460

Ile Leu Asp Ala Ala Glu Glu Ala Gly Leu Asp Leu Pro Tyr Ser Cys
465                 470                 475                 480

Arg Ala Gly Ala Cys Ser Thr Cys Ala Gly Lys Ile Thr Ala Gly Ser
            485                 490                 495

Val Asp Gln Ser Asp Gln Ser Phe Leu Asp Asp Asp Gln Ile Glu Ala
            500                 505                 510

Gly Tyr Val Leu Thr Cys Val Ala Tyr Pro Thr Ser Asp Cys Thr Ile
        515                 520                 525

Glu Thr His Lys Glu Glu Glu Leu Thr Ala
    530                 535
```